US007645449B2

(12) United States Patent
Stassi et al.

(10) Patent No.: US 7,645,449 B2
(45) Date of Patent: Jan. 12, 2010

(54) SENSITIZING CELLS FOR APOPTOSIS BY SELECTIVELY BLOCKING CYTOKINES

(76) Inventors: Giorgio Stassi, Dipartimento di Discipline Chirugiche ed, Oncologiche Cellulare e Molecolare, Via del Vespro, 129, IT-90127 Palermo (IT); Matilde Todaro, Dipartimento di Discipline Chirugiche ed, Oncologiche, Laboratorio di Fisiopatologia, Cellulare e Molecolare, Via del Vespro, 129, IT-90127 Palermo (IT)

( * ) Notice: Subject to any disclaimer, the term of this patent is extended or adjusted under 35 U.S.C. 154(b) by 277 days.

(21) Appl. No.: 10/544,794

(22) PCT Filed: Feb. 9, 2004

(86) PCT No.: PCT/EP2004/001177

§ 371 (c)(1),
(2), (4) Date: May 8, 2006

(87) PCT Pub. No.: WO2004/069274

PCT Pub. Date: Aug. 19, 2004

(65) Prior Publication Data

US 2006/0257401 A1    Nov. 16, 2006

(30) Foreign Application Priority Data

Feb. 7, 2003    (EP)    ................... 03002603

(51) Int. Cl.
*A61K 39/395* (2006.01)
*C12Q 1/68* (2006.01)

(52) U.S. Cl. .............. 424/130.1; 435/6; 435/7.23; 514/44; 514/2

(58) Field of Classification Search ................. None
See application file for complete search history.

(56) References Cited

U.S. PATENT DOCUMENTS

| | | | |
|---|---|---|---|
| 5,710,023 A | 1/1998 | Collins et al. | |
| 6,168,791 B1 | 1/2001 | Larsen et al. | |
| 6,534,051 B1 * | 3/2003 | Dornburg | ................ 424/93.2 |
| 6,548,655 B1 | 4/2003 | Mosley et al. | |
| 6,664,227 B1 | 12/2003 | Wynn et al. | |
| 2005/0232922 A1 | 10/2005 | Coggin, Jr. et al. | |

FOREIGN PATENT DOCUMENTS

| | | |
|---|---|---|
| WO | WO 89/09621 A2 | 10/1989 |
| WO | WO 96/04388 A1 | 2/1996 |
| WO | WO 97/38089 A1 | 10/1997 |
| WO | WO 98/47516 A1 | 10/1998 |
| WO | WO 99/63975 A2 | 12/1999 |
| WO | WO 00/04901 A1 | 2/2000 |
| WO | WO 00/36103 A1 | 6/2000 |
| WO | WO 01/74388 A1 | 10/2001 |
| WO | WO 02/04009 A2 | 1/2002 |
| WO | WO 02/089832 A2 | 11/2002 |
| WO | WO 03/099312 A1 | 12/2003 |
| WO | WO 2004/032951 A1 | 4/2004 |

OTHER PUBLICATIONS

Planting et al., Ann. Oncol. Jun. 1999;10(6):693-700.*
Lu et al., *Blood*, 1995, vol. 86, pp. 3123-3131.
Mainou-Fowler et al., *Leukemia and Lymphoma*, 1996, vol. 21, pp. 369-377.
Stassi et al., *Nature Reviews Immunology*, 2002, vol. 2, pp. 195-204.
Brummelkamp et al., *Science*, 2002, vol. 296, pp. 550-553.
Dinarello, *Nature Medicine*, 2003, vol. 9, pp. 20-22.
Economides et al., *Nature Medicine*, 2003, vol. 9, pp. 47-52.
Hellman, *Principles and Practice of Oncology*, Chapter 16, pp. 265-306, Devita et al., ed., 4th ed., 1993.
Lømo et al., *Blood*, vol. 89, No. 12, 1997, pp. 4415-4424.
Ning et al., *European Journal of Immunology*, vol. 26, No. 10, 1996, pp. 2356-2363.
Oppenheim, *International Journal of Hematology*, vol. 74, No. 1, 2001, pp. 3-8.
Stassi et al., *Cancer Research*, vol. 63, No. 20, 2003, pp. 6784-6790.
Stassi et al., *Nature Immunology*, vol. 1, No. 6, 2000, pp. 483-488.
Alas, Steve et al.; "Inhibition of Interleukin 10 by Rituximab Results in Down-Regulation of Bcl-2 and Sensitization of B-cell Non-Hodgkin''s Lymphoma to Apoptosis"; 2001, *Clinical Cancer Research*, vol. 7, pp. 709-723.
Borish, Larry C. et al.; "Interleukin-4 Receptor in Moderate Atopic Asthma"; 1999, *American Journal of Respiratory and Critical Care Medicine*, vol. 160, pp. 1816-1823.
Czarneski, J. et al.; "Studies in NZB IL-10 knockout mice of the requirement of IL-10 for progression of B-cell lymphoma"; 2004, *Leukemia*, vol. 18, pp. 597-606.
Kruse, Susanne et al.; "Characterization of the membrane-bound and a soluble form of human IL-4 receptor α produced by alternative splicing"; 1999, *International Immunology*, vol. 11, No. 12, pp. 1965-1969.
Hassuneh, Mona R. et al.; "Evidence for the Participation of Interleukin-2 (IL-2) and IL-4 in the Regualtion of Autonomous Growth and Tumorigenesis of Transformed Cells of Lymphoid Origin"; 1997, *Blood*, vol. 89, No. 2, pp. 610-620.
Camp, Benjamin J. et al.; "In Situ Cytokine Production by Breast Cancer Tumor-Infiltrating Lymphocytes"; 1996, *Annals of Surgical Oncology*, vol. 3, No. 2, pp. 176-184.
Dole, Mukund G. et al.; "Bcl-$x_L$ Is Expressed in Neuroblastoma Cells and Modulates Chemotherapy-Induced Apoptosis"; 1995, *Cancer Research*, vol. 55, pp. 2576-2582.
Sumitomo, Makoto et al.; "Induction of Apoptosis of Cytokine-Producing Bladder Cancer Cells by Adenovirus-Mediated $I_{\kappa}B_{\alpha}$ Overexpression"; 1999, *Human Gene Therapy*, vol. 10, pp. 37-47.
Wise, Gilbert J. et al.; "Cytokine Variations in Patients with Hormone Treated Prostate Cancer"; 2000, *The Journal of Urology*, vol. 164, pp. 722-725.

* cited by examiner

*Primary Examiner*—Misook Yu
(74) *Attorney, Agent, or Firm*—Townsend and Townsend and Crew LLP; Siegfried J. W. Ruppert

(57) ABSTRACT

The invention refers to the use of a cytokine antagonist which modulates the expression and/or the function of a cytokine, particularly a Th2 helper cell cytokine, in a cell and causes the down-regulation of anti-apoptotic proteins in said cell through the cytokine modulation for sensitizing cells for apoptosis. In particular, the cells that can be treated with the cytokine antagonists are drug-resistant cancer cells which fail to undergo apoptosis.

64 Claims, 17 Drawing Sheets

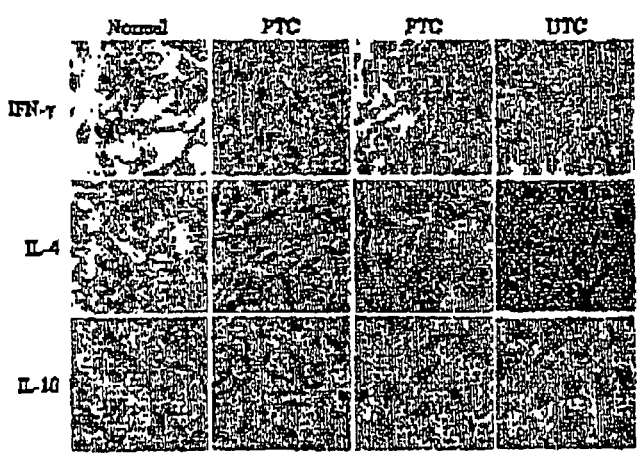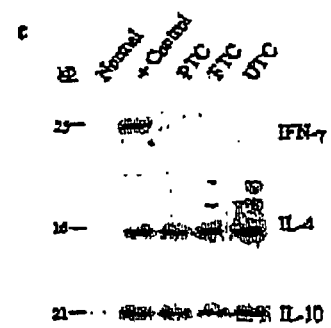
Figure 4b,c

A

B

C  D

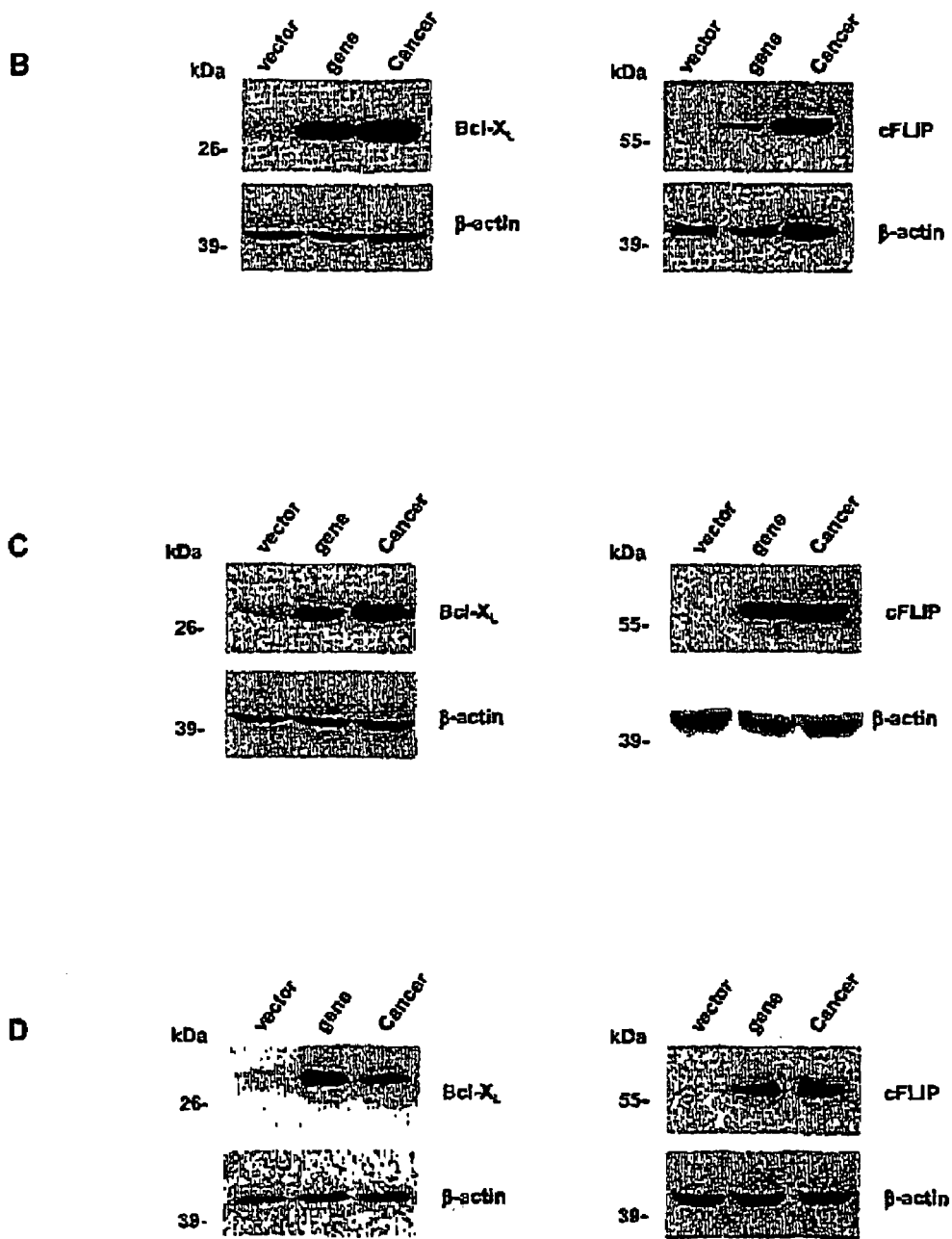
Fig. 13 B, C, D

SENSITIZING CELLS FOR APOPTOSIS BY SELECTIVELY BLOCKING CYTOKINES

This application is a U.S. National Phase of PCT/EP04/01177, filed May 8, 2006, which claims the benefit of European patent application No. 03002603.3, filed on Feb. 7, 2003, the disclosures of which are incorporated by reference herein in their entirety.

The present invention relates to a method of sensitizing cells for apoptosis by using compounds that selectively block cytokines, in particular interleukins, and the use of said compounds for the treatment of cancer and autoimmune diseases.

The molecular mechanisms controlling the balance between cell survival and cell death play a key role in a number of physiological and pathological processes. Crucial for the cellular ability to induce death of supernumerary, misplaced or damaged cells with high specificity and efficiency is the machinery of so-called "apoptosis" or "programmed cell death".

Diseases and conditions in which apoptosis has been implicated fall into two categories, those in which there is increased cell survival (i.e. apoptosis is reduced) and those in which there is excess cell death (i.e. apoptosis is increased). Diseases in which there is an excessive accumulation of cells due to increased cell survival include cancer, autoimmune disorders and viral infections. For these and other conditions in which insfficient apoptosis is believed to be involved, promotion of apoptosis is desired. This can be achieved, for example, by promoting cellular apoptosis or by increasing the sensitivity of cells to endogenous or exogenous apoptotic stimuli, for example, cell signaling molecules or other cytokines, cytotoxic drugs or radiation. Promotion of or sensitization to apoptosis is believed to have clinical relevance in sensitizing cancer cells to chemotherapeutic drugs or radiation.

In the second category, AIDS and neurodegenerative disorders like Alzheimer's or Parkinson's disease represent disorders for which an excess of cell death due to promotion of apoptosis (or unwanted apoptosis) is likely to be involved. Amyotrophic lateral sclerosis, retinitis pigmentosa, and epilepsy are other neurologic disorders in which apoptosis has been implicated. Apoptosis has been reported to occur in conditions characterized by ischemia, e.g. myocardial infarction and stroke. For these and other diseases and conditions in which unwanted apoptosis is believed to be involved, inhibitors of apoptosis are desired.

Currently, a major treatment for cancerous tumors is surgical removal of the affected areas of the tissue, organ, or gland. However, high recurrence rates are a major obstacle to the complete eradication of cancerous cells. It is believed that although the cancer cells in the malignant tumors can be removed surgically, cancerous cells that have invaded the surrounding tissue or lymph nodes frequently cause tumor recurrence. One reason for frequent tumor recurrence may be that during the development of the primary cancer, complete removal of all the cancer cells by surgical procedures is extremely difficult. Although irradiation, chemotherapy and appropriate hormone therapy all induce apoptosis to some extent in tumor cells, higher doses of the drugs or radiation may be required for suppressing the growth of cancer cells, which, in turn, can cause severe side effects on patients.

Thus, the problem underlying the present invention refers to the identification of compounds that specifically modulate distinct steps in the apoptosis pathway without causing the described deleterious side effects.

The effective cure of patients suffering from cancer is often difficult since many tumor cells have developed a resistance to anti-cancer drugs used for chemotherapy. The described phenotype involves a variety of strategies that tumor cells use to evade the cytostatic effects of anti-cancer drugs. Mechanisms for drag resistance include modifications in detoxification and DNA repair pathways, changes in cellular sites of drug sequestration, decreases in drug-target affinity, synthesis of specific drug inhibitors within cells, and accelerated removal or secretion of drugs. In addition, cancer cells commonly fail to undergo apoptosis. Thus, apoptosis defects appear to be a major problem in cancer therapy as they confer resistance to many tumors against current treatment protocols, leading to tumor progression.

Apoptosis pathways involve diverse groups of molecules. One set of mediators implicated in apoptosis are so-called caspases, cysteine proteases that cleave their substrate specifically at aspartate residues. Caspases convey the apoptic signal in a proteolytic cascade, with caspases cleaving and activating other caspases which subsequently degrade other cellular targets eventually resulting in cellular breakdown. Caspase activation itself can be triggered by external stimuli affecting certain self-surface receptors, known to the person skilled in the art as so-called death receptors, or by intracellular stress response via the mitochondria leading to the release of mitochondrial proteins. Known death receptors mediating apoptosis include members of the tumor necrosis factor (TNF) receptor super family such as, e.g. CD95 (APO-1/Fas) or TRAIL (TNF-related apoptosis inducing ligand) receptors 1 and 2. Stimulation of death receptors with apoptosis-inducing substances leads, among others, to the activation of caspase 8, which in turn activates other downstream-acting caspases.

The induction or inhibition of apoptosis is controlled in part by the Bcl-2 family members. A number of such genes, including Bcl-2 and Bcl-$x_L$, counteract apoptosis by preserving mitochondrial membrane integrity and preventing cytochrome c release in the cytoplasm. In contrast, the pro-apoptotic members such as Bax and Bad antagonize the function of Bcl-2 and Bcl-$X_L$ inducing heterodimer formation and mitochondrial membrane permeabilization with cytochrome c release.

In human cancers, a high expression of the anti-apoptotic members of the Bcl-2 family is commonly found and contributes to both neoplastic cell expansion and resistance to the therapeutic action of chemotherapeutic drugs. Overexpression of Bcl-2 can render cells resistant to apoptosis, thereby favoring malignant growth. Moreover, since -many chemotherapeutic agents kill tumor cells by inducing apoptosis, overexpression of Bcl-2 or Bcl-$x_L$ can lead to a multi-drug resistant phenotype.

The expression of a variety of genes involved in the survival or death of different target cells, including members of the Bcl-2 family, is regulated by so-called cytokines. Cytokines belong to a diverse group of soluble, non-antibody proteins secreted by a variety of cell types of the immune system, which modulate the functional activities of individual cells by interaction with specific cell surface receptors, e.g. interferon, interleukin. The person skilled in the art knows two functionally distinct subsets of so-called T-helper cells that have been characterized on the basis of cytokine production. One subset, Th1 cells, secrete IFN-γ and other cytokines associated with inflammation and cell-mediated immune responses, whereas Th2 cells promote humoral response releasing IL-4, IL-5 and IL-10.

It is known in the art that cancer types of lymphoid origin (and probably also of myeloid origin) autocrinely produce cytokines such as IL-1 and IL-6, and that. e.g. IL-4 enhances the survival of B cells in chronic lymphocytic leukaemia (CLL) in vitro by inhibiting apoptosis (see e.g. Lu Zhao Yan et al., Blood, 1995, Vol. 86, pages 3123-3131; Mainou-Fowler et al., Leukemia and Lymphoma, 1996, Vol. 21, pages 369-377). On the other hand, cytokines produced by T or B lymphocytes in the surrounding of a tumor, e.g. thyroid cancer, promote the survival and/or growth of said tumor (Stassi et al., Nature Reviews Immunology, 2002, Vol. 2, pages 195-204).

With respect to solve the problem underlying the present invention, namely the identification of compounds that specifically modulate distinct apoptosis steps, the inventors have surprisingly found that thyroid cancer cells autocrinely produce high levels of IL-4 and IL-10, as compared with normal tissues, while IFN-γ was barely detectable in those cancer cells. Thyroid cancer is the most common endocrine malignancy, responsible for about 60% of the death secondary to endocrine cancer. Three major types of malignant tumors originate from the thyroid epithelium. The more differentiated papillary (PTC) and follicular (FTC) thyroid carcinomas account for the vast majority of malignant tumors, while the undifferentiated anaplastic carcinomas (UTC) are extremely rare. The high levels of IL-4 and IL-10 in thyroid cancer cells correlated with an overexpression of Bcl-$x_L$ and Bcl-2 which in turn protects thyroid cancer cells against the cytotoxic effect of chemotherapeutic drugs suggesting a potential role of these anti-apoptotic proteins in thyroid cancer resistance from drug-induced cytotoxicity.

The person skilled in the art is aware of the fact that thyroid cancer cells belong to so-called epithelial cancers which are clearly distinguished from either lymphoid or myeloid cancer types.

Thus, a first object of the present invention refers to the use of a cytokine antagonist which modulates the expression and/or the function of a cytokine in a cell for the down-regulation of a cell death preventing protein in a cell.

As a result of the down-regulation of a cell death preventing protein the cell is sensitized for cell death. In the context of the present invention, the term "cell death" refers to any mechanism and process which can cause a cell to die. The skilled artisan distinguishes two processes named apoptosis and necrosis both of which are addressed within the scope of the present invention. However, the use of a cytokine antagonist according to the present invention is particularly effective if the death process the cell should be sensitized for is apoptosis. Thus, in a preferred embodiment of the present invention the "cell death preventing" proteins refer to "anti-apoptotic" proteins.

In a particular embodiment of the present invention the term "cell" refers to cells, that fail to undergo apoptosis as described in the introduction. In this respect, the cells encompass, for example, cancer cells and self-reacting cells of the immune system. Most preferably, the cell of the present invention is a cancer cell.

In a particularly preferred embodiment, the cancer cell is a non-lymphoid and/or a non-myeloid cancer cell, most preferably an epithelial cancer.

If the cell is a cancer cell, the defect in undergoing apoptosis may have rendered the cell resistant to various treatment strategies exploiting anti-neoplastic compounds and/or radiation therapies. The cancer cell to which the cytokine is preferably applied to can also be resistant to compounds which do not necessarily lead to cell death directly, but which sensitize these cells for apoptosis. The skilled artisan knows that such compounds include naturally occurring agonists for death receptors, i.e. receptor ligands or agonistic antibodies to said death receptors, as well as chemotherapeutic drugs.

The "cytokine" of the present invention belongs to the group of cytokines that are predominantly secreted by Th2 helper cells. More preferably, the cytokine is selected from the group consisting of IL-4, IL-5, IL-6, IL-10, and IL-13, as well as combinations thereof. For the efficient use of the cytokine antagonist of the present invention it is most preferred, if the cytokine is IL-4, IL-10 and/or IL-13, as well as combinations thereof.

Within the scope of the present invention, "anti-apoptotic proteins" include members of the Bcl family such as Bcl-2, Bcl-$x_L$, cFLIP, Mcl-1, Bcl-w, A1/BFL1, BOO/DIVA, NR-13, sentrin, TOSO, CPAN, PED, DFF45, and the like. The anti-apoptotic proteins of the present invention also include so-called "Inhibitors of Apoptosis Proteins" (IAPs). IAPs bind to early active caspases, thereby preventing the ongoing of the apoptosis process. They are expressed at high levels in many tumors and, by inhibition of caspases, contribute to the resistance of cancers against apoptosis induction. Examples of IAPs include NAIP, XIAP (hILP), cIAP-1, cIAP-2, ML-IAP (livin), KIAP, BIRC5 (survivin), TIAP, and Apollon. Finally, anti-apoptotic proteins can be others such as fortilin, and the like.

In a preferred embodiment of the present invention, the anti-apoptotic proteins include PED, cFLIP, Bcl-2 and Bcl-$x_L$, and combinations thereof. Most preferably, the anti-apoptotic proteins which are down-regulated by the cytokine antagonist are Bcl-2 and/or Bcl-$x_L$.

The term "cytokine antagonist" refers to any compound that is capable of directly modulating the expression and/or the function of the cytokine, thus leading to the down-regulation of anti-apoptotic proteins. It is further contemplated within the scope of the present invention that the cytokine antagonist refers to any compound that modulates the expression and/or the function of a cytokine indirectly, namely by affecting the expression and/or the function of the respective cytokine receptor. It is obvious to the person skilled in the art that a down-regulation of the cytokine receptor directly interferes with the function of the cytokine itself. Therefore, the hereinafter described mechanisms and molecules, respectively, that modulate the expression and/or the function of a cytokine may also be extrapolated to cytokine receptors. In this respect, the term "cytokine" encompasses also cytokine receptors, unless otherwise indicated.

In the context of the present invention, the modulation of the expression and/or the function of the cytokine/cytokine receptor, hereinafter referred to as the "modulation", by the use of the cytokine antagonist according to the present invention can occur on the protein and/or on the nucleic acid level.

If the modulation occurs on the nucleic acid level, the cytokine antagonist according to the present invention can be a peptide or a nucleic acid that regulates the transcription of the cytokine gene by binding to up-stream and/or down-stream regulatory sequences of the coding region of the cytokine. Such regulatory sequences are known to the person skilled in the art and include so-called promoter, operator, enhancer or silencer regions. For example, the cytokine antagonist may interfere with the binding of the RNA polymerase to the promoter region of the cytokine gene, either by binding directly to the RNA polymerase binding region, by binding to the polymerase itself or by binding to other factors, e.g. transcription factors, which are required for efficient RNA polymerase binding and function. Furthermore, the cytokine antagonist may bind to the operator region and act as a so-called repressor of cytokine gene expression.

In a further embodiment of the present invention, the modulation on the nucleic acid level can occur by the use of nucleic acid molecules that hybridize to, and are therefore complementary to the coding sequence of the cytokine. These nucleic acid molecules may encode or act as cytokine gene antisense molecules useful, for example, in cytokine gene regulation. With respect to cytokine gene regulation, such techniques can be used to modulate, for example, the phenotype and metastatic potential of cancer cells. The use of antisense molecules as inhibitors is a specific, genetically based therapeutic approach The present invention provides the therapeutic and prophylactic use of nucleic acids of at least six nucleotides that are antisense to a gene or cDNA encoding one of the aforementioned cytokines.

Similarly, a cytokine antagonist of the present invention that modulates the expression and/or the function of a cytokine on the nucleic acid level can be a dsRNA molecule which is complementary to the cytokine mRNA. Such molecules are also known in the art as small interfering RNA (siRNA). This technology to inhibit the expression of cerain mRNAs is known to the person skilled in the art as RNA interference (RNAi). Preferably, the dsRNA molecules which are complementary to the mRNA of the cytokines of the present invention have a length between 10 and 30 base pairs, more preferably, they have a length between 19 and 25 base pairs. The cytokine antagonist being siRNA may be delivered to the target cell by any method known to the one of skilled art. Applicable is, for instance, the delivery by using cationic liposome reagents. It is also conceivable that the siRNA directed against the cytokine mRNA is obtained by using the DNA encoding it. In this case, a DNA construct comprising both a stretch of 19 to 25 nucleotides of the desired cytokine coding region, and the antisense stretch being separated from the sense stretch by a suitable linker which is able to form a hairpin loop, is inserted into a vector. The vector can be introduced into the target cell by methods well known the skilled artisan. The design of such a construct is further described e.g. in Brummelkamp et al. (Science 2002 Vol. 296, pages 550-553).

Furthermore, the present invention encompasses so-called ribozymes as cytokine antagonists. Ribozymes are naturally occurring RNA fragments that can be designed as human therapeutics to recognize, bind and digest any disease-causing mRNA sequence, in this case the cytokine mRNA. Ribozymes are designed to target the cytokine mRNA through complementary base pair hybridization. After binding to the target, the enzymatic activity of the ribozyme cleaves the cytokine mRNA thus preventing its translation into protein. The cytokine mRNA ribozymes can be chemically synthesized to selectively inhibit the cytokine production. In addition, the ribozymes may be chemically modified allowing the ribozymes to be more stable and active. Included are also ribozymes that do not only cleave cytokine-specific RNA molecules but also form carbon-carbon bonds in a covalent fashion, which raises the possibility of ribozymes that can catalyze other types of chemical reactions.

In a further embodiment of the present invention the translation of the cytokine gene can be reduced or eliminated by binding of an RNA-binding protein to one or more operator sequences in the 5'-UTR of the cytokine mRNA transcript. The bound RNA-binding protein interferes with translation, likely by preventing ribosome assembly or blocking the movement of the ribosome along the transcript from 5' to 3'. Such RNA-binding proteins may be multimeric, e.g. dimers of a particular RNA-binding protein. It is also possible within the scope of the present invention that the cytokine antagonist inhibits the cytokine expression by promoting or at least being involved in the degradation of cytokine mRNA.

If the modulation occurs on the protein level, the present invention encompasses antibodies or fragments thereof capable of specifically recognizing one or more epitopes of the cytokine gene products, epitopes of conserved variants of the cytokine gene products, epitopes of mutant cytokine gene products, or peptide fragments of cytokine gene products. Such antibodies may include, but are not limited to, polyclonal antibodies, monoclonal antibodies (mAbs), human, humanized or chimeric antibodies, single-chain antibodies, Fab fragments, F(ab')2 fragments, Fv fragments, fragments produced by a Fab expression library, anti-idiotypic (anti-Id) antibodies, and epitope-binding fragments of any of the above. The cytokine antagonist being an antibody as described above can be used to capture and neutralize excessive amounts of cytokines that are overexpressed in drug-resistant cancer cells. It may be desirable for the present invention if the antibody recognizes more than one of the above mentioned cytokines. In order to capture and neutralize more than one overexpressed cytokine, the antibody used as a cytokine antagonist of the present invention can possess more than one specificities, i.e. being, for example, bispecific, trispecific or multispecific.

Epitopes and antigenic regions useful for generating antibodies can be found within the cytokine amino acid sequences (e.g. SWISS-PROT numbers P05112 for IL-4, P22301 for IL-10 or P35225 for IL-13) by procedures available to one of skill in the art. For example, short, unique peptide sequences can be identified in the amino acid sequences that have little or no homology to known amino acid sequences. Preferably the region of a protein selected to act as a peptide epitope or antigen is not entirely hydrophobic; hydrophilic regions are preferred because those regions likely constitute surface epitopes rather than internal regions of the present proteins and polypeptides. These surface epitopes are more readily detected in samples tested for the presence of the present proteins and polypeptides.

Peptides can be made by any procedure known to one of skill in the art, for example, by using in vitro translation or chemical synthesis procedures. Short peptides which provide an antigenic epitope but which by themselves are too small to induce an immune response may be conjugated to a suitable carrier. Suitable carriers and methods of linkage are well known in the art. Suitable carriers are typically large macromolecules such as proteins, polysaccharides and polymeric amino acids. Examples include serum albumins, keyhole limpet hemocyanin, ovalbumin, polylysine and the like. One of skill in the art can use available procedures and coupling reagents to link the desired peptide epitope to such a carrier. For example, coupling reagents can be used to form disulfide linkages or thioether linkages from the carrier to the peptide of interest. If the peptide lacks a disulfide group, one may be provided by the addition of a cysteine residue. Alternatively, coupling may be accomplished by activation of carboxyl groups.

The minimum size of peptides useful for obtaining antigen specific antibodies can vary widely. The minimum size must be sufficient to provide an antigenic epitope which is specific to the protein or polypeptide. The maximum size is not critical unless it is desired to obtain antibodies to one particular epitope. For example, a large polypeptide may comprise multiple epitopes, one epitope being particularly useful and a second epitope being immunodominant.

In a preferred embodiment of the present invention, the cytokine antagonist refers to an antibody against IL-4, IL-5, IL-6, IL-10, and/or IL-13, as well as combinations thereof. Even more preferred, the cytokine antagonist refers to an antibody against IL-4, IL-10, and/or IL-13, as well as combinations thereof. Most preferably, the cytokine antagonist refers to an antibody against IL-4 and/or IL-10, and combinations thereof It is understood that the antibody being used as a cytokine antagonist can possess more than one specificities, as described supra, i.e. being directed to more than one of the mentioned IL, e.g. abispecific antibody to IL4 and IL10.

In a further embodiment of the present invention, the cytokine antagonist that modulates the expression and/or the function of the cytokine can be a so-called aptamer, either a peptide-based aptamer or an oligonucleotide-based aptamer. Peptide aptamers are defined as protein-based recognition agents that consist of constrained combinatorial peptide libraries displayed on the surface of a scaffold protein. Peptide aptamers function in trans, interacting with and inactivating gene products without mutating the DNA that encodes them. In principle, combinatorial libraries of peptide aptamers should contain aptamers that interact with any given gene product, thus allowing peptide aptamers to be generated against an organism's entire proteome. Oligonucleotide-based aptamers being used as cytokine antagonist according to the present invention comprise DNA as well as RNA aptamers. In this respect, the present invention encompasses also mirror-image L-DNA or L-RNA aptamers, so-called spiegelbners.

The aptamers that are useful as cytokine antagonists for the present invention include those which interact with specific proteins and thus prevent or disrupt the specific protein interaction between the cytokine and its receptor. They can interact with the cytokine itself, preferably with that region of the cytokine that is involved in the receptor binding. The aptamers can also prevent/disrupt the interaction between the cytokine and its receptor by binding to the receptor, preferably with that region of the receptor that is involved in the cytokine binding. It is also possible that the aptamers bind to other factors/proteins that are required for successful cytokine/receptor interaction.

In the context of the described aptamers, it is also feasable the the cytokine antagonist comprises so-called small molecule inhibitors that may exhibit similar properties as aptamers, namely binding to either the cytokine or to the cytokine receptor, thereby inhibiting their proper interaction and, thus, function. The small molecule inhibitor can be a peptide or a small chemical compound, which has been identified by methods known to the skilled artisan, e.g. by computational combinatorial chemistry in combination with screening of compound libraries.

In a further embodiment of the present invention the cytokine antagonist that modulates the expression and/or the function of the cytokine, comprises at least one receptor, a derivative or fragment thereof, of any of the cytokines included in the present invention. Similarly to the proposed and described effect for using antibodies as cytokine antagonists, the cytokine receptor, a fragment or derivative thereof, can be used to capture and neutralize excessive amounts of cytokines which are overexpressed in drug-resistant cancer cells. Examples for suitable receptors and receptor subunits, respectively, include CD124 which binds both IL-4 and IL-13 (data base accession number P24394), CD132 which represents the common gamma subunit shared by IL-2, IL-4, IL-7, IL-9, and IL-15 receptors (data base accession number P31785), IL-13 receptor alpha-2 chain (data base accession number Q14627) and IL-10 receptor alpha chain (database accession number Q13651).

In the context of the present invention the term "derivative or fragment" of a cytokine receptor refers to peptides the length of which and/or the amino acid composition of which can differ from the originally disclosed amino acid sequence, provided that the function of the receptor, namely the binding of the cytokine, is neither reduced nor eliminated. Therefore, the term "derivative or fragment" includes peptides which are extended or shortened on either the amino- or the carboxy-terminal end or which possess deletions or insertions internally. In addition, the term "derivative or fragment" includes peptides with one or more amino acids being different from the originally disclosed sequence. Particularly advantageous for the present invention, especially if the receptor is used therapeutically, are soluble receptors lacking the transmembrane region. In this case, the receptor comprises the proposed extracellular binding domain, a fragment or derivative thereof, optionally being directly or via a spacer linked to the proposed intracellular domain or to the Fc part of an antibody.

With respect to receptors, derivatives or fragments thereof, the present invention also comprises so-called cytokine traps, which make use of the fact that the signalling cascade triggered by cytokines is initiated with the cytokine binding to a first subunit, said binding leading to the recruitment of the second subunit, whereby only the complex of the cytokine bound to both receptor subunit chains initiate the subsequent cascade. As described in Nature Medicine 2003, Vol. 9, pages 20-22 and pages 47-52, cytokine traps consist of the two relevant receptor subunits which are linked together by fusion with the Fc portion (complement binding domain) of the immunoglobulin IgG1. Therefore, the cytokine antagonist of the present invention can be a so-called "heterodimeric trap" consisting of two receptor subunits each of which is fused to the Fc portion of an antibody comprising the heavy chain constant regions CH2 and CH3 and the hinge region of IgG1, whereby the constructs are paired via disulfide bridges between the hinge regions. The cytokine antagonist of the present invention can also be a so-called "inline trap", where the two receptor extracellular domains are fused in-line followed by the human IgG1 Fc. For example, a cytokine antagonist for the cytokine IL-4 would consist of the extracellular domains of CD124, as specified above, and CD132, as specified above, linked to IgG1 in the described manner.

Furthermore, the modulation of the cytokine can be achieved by using so-called muteins of the cytokines. Muteins are derivatives of biologically active proteins the amino acid composition of which has been artificially altered. The muteins of the present invention are still able to bind to their respective cell surface receptor, but are incapable of triggering an internal signal cascade which would lead to the up-regulation of anti-apoptotic proteins. In this respect, the muteins compete with the endogenously expressed cytokines for the binding sites on the respective receptor. The muteins can be made via bacterial expression of mutant genes that encode the muteins that have been synthesized from the genes for the parent proteins by oligonucleotide-directed mutagenesis.

In line with the above disclosures, the present invention furthermore refers to a method for the down-regulation of a cell death preventing protein in a cell, the method comprising
 (a) providing a sample of tissue or cells from a subject
 (b) contacting the cell or the sample with a cytokine antagonist In a particularly preferred embodiment of the present invention the cell, to which the disclosed method should be applied to, is a cancer cell.

In a particular embodiment, the present invention refers to a method for the down-regulation of an anti-apoptotic protein in a non-lymphoid and/or non-myeloid cancer target cell which autocrinely produces high levels of a cytokine, preferably an interleulin, the method comprising contacting the target cell or the sample with a cytokine antagonist as defined supra.

In order to act properly as a cytokine antagonist and in order to perform the described method it is desirable that the cytokine antagonist is delivered to the site of action namely to the proximity of a cell and/or into a cell. The person skilled in the art is aware of a variety of methods how to deliver the disclosed cytokine antagonists into or in the proximity of the target cell. In general, the appropriate method depends on whether the cytokine antagonist is a nucleic acid or a peptide. Furthermore, if the cytokine antagonist is a peptide it can be delivered into or in the proximity of the target cell by introducing the nucleic acid encoding it either to the target cell itself or to other cells being suitable to produce the peptide. For peptide production, both eukaryotic and prokaryotic host cells are contemplated.

There are several well-known methods of introducing nucleic acids into animal cells, any of which may be used in the present invention and which depend on the host. Typical hosts include mammalian species, such as humans, non-human primates, dogs, cats, cattle, horses, sheep, and the like. At the simplest, the nucleic acid can be directly injected into the target cell/target tissue, or by so-called microinjection into the nucleus. Other methods include fusion of the recipient cell with bacterial protoplasts containing the nucleic acid, the use of compositions like calcium chloride, rubidium chloride, lithium chloride, calcium phosphate, DEAE dextran, cationic lipids or liposomes or methods like receptor-mediated endocytosis, biolistic particle bombardment ("gene gun" method), infection with viral vectors, electroporation, and the like.

For the introduction of the cytokine antagonist, respectively the nucleic acid encoding it, into the cell and its expression it can be advantageous if the nucleic acid is integrated in an expression vector. The expression vector is preferably a eukaryotic expression vector, or a retroviral vector, a plasmid, bacteriophage, or any other vector typically used in the biotechnology field If necessary or desired, the nucleic acid encoding the cytokine antagonist can be operatively linked to regulatory elements which direct the transcription and the synthesis of a translatable mRNA in pro- or eukaryotic cells. Such regulatory elements are promoters, enhancers or transcription termination signals, but can also comprise introns or similar elements, for example those, which promote or contribute to the stability and the amplification of the vector, the selection for successful delivery and/or the integration into the host's genome, like regions that promote homologous recombination at a desired site in the genome. For therapeutic purposes, the use of retroviral vectors has been proven to be most appropriate to deliver a desired nucleic acid into a target cell.

If the cytokine antagonist is a peptide that shall be directly introduced into the target cell it can be fused to a carrier peptide that mediates the cellular uptake of the peptide. Appropriate carriers are known to the person skilled in the art and include TAT, fibroblast growth factor, galparan (transportan), poly-arginine, and Pep-1, and functional fragments and derivatives of any of said carriers. Furthermore, the cytokine may be fused to a ligand for a cell surface receptor, or a functional portion thereof, and thus internalized by receptor-mediated endocytosis.

The cytokine antagonist as disclosed in the present invention can be used as a pharmaceutical, optionally in combination with at least one active compound, for the treatment of cancer. This is a further embodiment of the present invention. The term "active compound" refers to a compound other than the cytokine antagonist which is able to induce or sensitize for cell death, preferably apoptosis, or which inhibits cell proliferation. Active compounds which are able to induce or sensitize for cell death, preferably apoptosis are known to the person skilled in the art.

First the phrase "active compound" refers to the use of electromagnetic or particulate radiation in the treatment of neoplasia Radiation therapy is based on the principle that high-dose radiation delivered to a target area will result in the death of reproductive cells in both tumor and normal tissues. The radiation dosage regimen is generally defined in terms of radiation absorbed dose (rad), time and fractionation, and must be carefully defined by the oncologist The amount of radiation a patient receives will depend on various consideration but the two most important considerations are the location of the tumor in relation to other critical structures or organs of the body, and the extent to which the tumor has spread. Examples of radiotherapeutic agents are provided in, but not limited to, radiation therapy and is known in the art (Hellman, Principles of Radiation Therapy, Cancer, in Principles and Practice of Oncology, 24875 (Devita et al., ed., 4th ed., v1, 1993). Recent advances in radiation therapy include three-dimensional conformal external beam radiation, intensity modulated radiation therapy (IMRT), stereotactic radiosurgery and brachytherapy (interstitial radiation therapy), the latter placing the source of radiation directly into the tumor as implanted "seeds." These newer treatment modalities deliver greater doses of radiation to the tumor, which accounts for their increased effectiveness when compared to standard external beam radiation therapy. Beta-emitting radionuclides are considered the most useful for radiotherapeutic applications because of the moderate linear energy transfer (LET) of the ionizing particle (electron) and its intermediate range (typically several millimeters in tissue). Gamma rays deliver dosage at lower levels over much greater distances. Alpha particles represent the other extreme; they deliver very high LET dosage, but have an extremely limited range and must, therefore, be in intimate contact with the cells of the tissue to be treated. In addition, alpha emitters are generally heavy metals, which limits the possible chemistry and presents undue hazards from leakage of radionuclide from the area to be treated. Depending on the tumor to be treated all kinds of emitters are conceivable within the scope of the present invention.

Generally, radiation therapy can be combined temporally with other active compounds listed below to improve the outcome of treatment. There are various terms to describe the temporal relationship of administering radiation therapy together with other active compounds, and the following examples are the preferred treatment regimens and are generally known by those skilled in the art and are provided for illustration only and are not intended to limit the use of other combinations. Administration of radiation therapy with other active compounds can be "sequential", i.e. separately in time in order to allow the separate administration, "concomitant" which refers to the administration on the same day, and, finally, "alternating" which refers to the administration of radiation therapy on the days in which other active compounds would not have been administered.

Another class of active compounds are chemical compounds having a cytostatic or anti-neoplastic effect ("cytostatic compound"). Cytostatic compounds included in the present invention comprise, but are not restricted to (i) antimetabolites, such as cytarabine, fludarabine, 5-fluoro-2'-deoxyuiridine, gemcitabine, hydroxyurea or methotrexate; (ii) DNA-fragmenting agents, such as bleomycin, (iii) DNA-crosslinking agents, such as chlorambucil, cisplatin, cyclophosphamide or nitrogen mustard; (iv) intercalating agents such as adriamycin (doxorubicin) or mitoxantrone; (v) protein synthesis inhibitors, such as L-asparaginase, cyclohex-imide, puromycin or diphteria toxin; (vi) topoisomerase I poisons, such as camptothecin or topotecan; (vii) topoi-somerase II poisons, such as etoposide (VP-16) or teniposide; (viii) microtubule-directed agents, such as colcemid, colchi-cine, paclitaxel, vinblastine or vincristine; (ix) kinase inhibi-tors such as flavopiridol, staurosporin, STI571 (CPG 57148B) or UCN-01 (7-hydroxystaurosporine); (x) miscella-neous investigational agents such as thioplatin, PS-341, phe-nylbutyrate, ET-18-OCH$_3$, or farnesyl transferase inhibitors (L-739749, L-744832); polyphenols such as quercetin, res-veratrol, piceatannol, epigallocatechine gallate, theaflavins, flavanols, procyanidins, betulinic acid and derivatives thereof; (xi) hormones such as glucocorticoids or fenretinide; (xii) hormone antagonists, such as tamoxifen, finasteride or LHRH antagonists.

Other cytostatic compounds include plant-derived cyto-statics (from Viscum and derivatives); alcaloids such as vin-desine; podophyllotoxins such as vinorelbin; alkylants such as nimustrine, carmustrine, lomustine, estramustrine, mel-phalam, ifosfamide, trofosfamide, bendamustine, dacarba-zine, busulfane, procarbazine, treosulfane, tremozolamide, thiotepa; cytotoxic antibiotics such as aclarubicine, daunoru-bicine, epirubicine, idarubicine, mitomycine, dactinomycine; antimetabolites like folic acid analogs such as methotrexate, purine analogs such as cladribin, mercaptopurin, tioguanine and pyrimidine analogs such as cytarabine, fluorouracil, doc-etaxel; platinum compounds such as carboplatin, oxaliplatin; amsacrine, irinotecane, interferon-α, tretinoine, hydroxycar-bamide, miltefosine, pentostatine, aldesleukine; antineoplas-tic compounds derived from organs, e.g. monoclonal antibod-ies such as trastuzumab, rituximab, or derived from enyzmes such as pegaspargase; endocrine effecting antineoplastic compounds belonging to hormones, e.g. estrogens such as polyestradiol, fosfestriol, ethinylestradiol, gestagens such as medroxyprogesterone, gestonoroncaproat, megestrol, nore-thisterone, lynestrenol, hypothalamus hormones such as trip-toreline, leuproreline, busereline, gosereline, other hormones such as testolactone, testosterone; endocrine effecting anti-neoplastic compounds belonging to hormone antagonists, e.g. antiestrogens such as toremifen; antiandrogens such as flutamide, bicalutamide, cyproterane; endocrine effecting antineoplastic compounds belonging to enzyme inhibitors such as anastrol, exemestane, letrozol, formestane, aminoglu-tethimide, all of which can be occasionally administered together with so-called protectives such as calciumfolinat, amifostin, lenograstin, molgromostin, filgrastin, mesna or so-called additives such as retinolpahnitate, thymus D9, amilomer.

In a preferred embodiment of the present invention, the active compound having a cytostatic effect is selected from the group consisting of cisplatin, doxorubicin and paclitaxel (taxol).

Another class of active compounds which can be used in the present invention are those which are able to sensitize for or induce apoptosis by binding to death receptors ("death receptor agonists"). Agonists of death receptors include death receptor ligands such as tumor necrosis factor α (TNF-α), tumor necrosis factor β (TNF-β, lymphotoxin-α), LT-β (lym-photoxin-β), TRAIL (Apo2L, DR4 ligand), CD95 (Fas, APO-1) ligand, TRAMP (DP3, Apo-3) ligand, DR6 ligand as well as fragments and derivatives of any of said ligands. Further-more, death receptors agonists comprise agonistic antibodies to death receptors such as anti-CD95 antibody, anti-TRAIL-R1 (DR4) antibody, anti-TRAIL-R2 (DR5) antibody, anti-DR6 antibody, anti TNF-R1 (p55 TNF-R) antibody and anti-TRAMP (DR3) antibody as well as fragments and derivatives of any of said antibodies. Preferably, the agonistic antibodies are selected from the group consisting of anti-TRAIL-R1 antibody, anti-TRAIL-R2 antibody, anti TNF-R1 antibody and fragments and derivatives of any of said antibodies.

Another class of active compounds which can be used in combination with the cytokine antagonist are peptides, pro-teins or small molecule inhibitors which negatively regulate or inhibit the above described anti-apoptotic proteins. Examples of negatively regulating peptides include Smac/DIABLO, NRAGE and TAK1, fragments and derivatives thereof, which particularly inhibit the above described IAPs. These peptides may be modified in a way that they can be rapidly internalized into tumor cells by cellular uptake. The modification can occur by attaching a carrier peptide that mediates cellular uptake as disclosed above to the active compound.

The cytokine antagonist can be administered alone or in combination with one or more active compounds. The latter can be administered before, after or simultaneously with the administration of the cytokine antagonist. The dose of either the cytokine antagonist or the active compound as well as the duration and the temperature of incubation can be variable and depends on the target that is to be treated.

A further object of the present invention are pharmaceuti-cal preparations which comprise an effective dose of at least one cytokine antagonist, optionally in combination with at least one active compound and a pharmaceutically acceptable carrier, i.e. one or more pharmaceutically acceptable carrier substances and/or additives.

The pharmaceutical according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscu-larly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administra-tion form depends, for example, on the disease to be treated and on its severity.

The preparation of the pharmaceutical compositions can be carried out in a manner known per se. To this end, the cytokine antagonist and/or the active compound, together with one or more solid or liquid pharmaceutical carrier substances and/or additives (or auxiliary substances) and, if desired, in combi-nation with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules it is possible to use, for example, lac-tose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiological sodium chloride solution, alcohols such as ethanol, glycerol, polyols, sucrose, invert sugar, glucose, mannitol, vegetable oils, etc. It is also possible to lyophilize the cytokine antagonist and/or the active com-pound and to use the resulting lyophilisates, for example, for preparing preparations for injection or infusion. Suitable car-riers for microcapsules, implants or rods are, for example, copolymers of glycolic acid and lactic acid.

The pharmaceutical preparations can also contain addi-tives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the cytokine antagonist, in combination with one or more active compounds to be administered, depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to the cytokine antagonist.

The cytokine antagonists according to the present invention, respectively the medicaments containing the latter, can be used for the treatment of all cancer types which are resistant to apoptosis due to the expression of anti-apoptotic proteins. Examples of such cancer types comprise neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, follicular thyroid carcinoma, anaplastic thyroid carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeolid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma and plasmocytoma.

In a particularly preferred embodiment, the cytokine antagonists according to the present invention, respectively the medicaments containing the latter, can be used for the treatment of non-lymphoid and non-myeloid, preferably epithelial cancers.

Examples of cancer types where the use of the cytokine antagonists according to the present invention, respectively the medicaments containing the latter, is particularly advantageous include all forms of thyroid carcinomas (medullary thyroid carcinoma, papillary thyroid carcinoma, follicular thyroid carcinoma, anaplastic thyroid carcinoma), breast carcinoma, lung carcinoma, prostate carcinoma and colon carcinoma. Most preferably, the cytokine antagonists are useful for the treatment of thyroid carcinomas.

The cytokine antagonists according to the present invention, respectively the medicaments containing the latter, can also be used for the treatment of all autoimmune diseases which are resistant to apoptosis due to the expression of anti-apoptotic proteins. Examples of such autoimmune diseases are collagen diseases such as rheumatoid arthritis, Lupus erythematodes disseminatus, Sharp syndrome, CREST syndrome (calcinosis, Raynaud syndrome, esophageal dysmotility, teleangiectasia), dermatomyositis, vasculitis (Morbus Wegener) and Sjögren syndrome, renal diseases such as Goodpasture syndrome, rapidly-progressing glomerulonephritis and membrane-proliferative glomerulonephritis type II, endocrine diseases such as type-I diabetes, autoimmune polyendocrinopathy-candidiasis-ectodermal dystrophy (APECED), autoimmune parathyreoidism, pernicious anemia, gonad insnfficiency, idiopathic Morbus Addison, hyperthyreosis, Hashimoto thyroiditis and primary myxedemia, skin diseases such as Pemphigus vulgaris, bullous pemphigoid, Herpes gestationis, Epidermolysis bullosa and Erythema multifonme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, Myastenia gravis, myasthenic Lambert-Eaton syndrome, acquired neuromyotony, Guiliain-Barré syndrome (Mfller-Fischer syndrome), Stiff-man syndrome, cerebellar degeneration, ataxia, opsoldonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, Malaria and Chagas disease.

A further object of the present invention is the use of the cytokine antagonist hybridizing with or binding to the cytokine, or the nucleic acid encoding it, as a diagnostic tool to detect and quantify the expression level of a cytokine present in the drug-resistant tumor cell. It is also possible to detect and quantify the expression level of a cytokine and thus, the susceptibility for cancer, by analyzing any of a potential patient's body fluid, such as serous effusions (blood), semen, vaginal secretions, saliva, cerebrospinal fluid, pleural and pericardial fluid, peritoneal fluid, synovial fluid and anmiotic fluid.

Thus, the present invention refers to the use of a cytokine antagonist for diagnosing and monitoring the cancer disease of a subject, comprising
  (a) providing a body fluid sample or a sample of tissue or cells from a non-lymphoid and/or non-myeloid tumor of a subject
  (b) contacting the sample with a labeled probe that binds to a cytokine nucleic acid and/or with an antibody that binds to a cytokine
  (c) determining the expression level of the cytokine in the tissue or cells and comparing the expression level with healthy control cells, and
  (d) correlating a better prognosis for the subject with a low ratio of cytokine expression when compared to the expression level in healthy control cells.

The cytokine antagonist may therefore be usefil to predict whether a patient suffering from a certain cancer type would be susceptible to a certain therapy and whether it would be required to change the treatment strategies. Binding and hybridization assays can be used to detect, prognose, diagnose, or monitor disease (including conditions and disorders) associated with the overexpression of the cytolines in tumor cells or body fluids. This requires the detection of nucleic acids that encode the cytokines, and the detection of the cytokine proteins.

Cytokine nucleic acids are detected and quantified herein by any of a number of means well known to those of skill in the art. Appropriate detection methods include biochemical methods such as spectrophotometry, radiography, gel electrophoresis, capillary electrophoresis, high performance liquid chromatography (HPLC), thin layer chromatography (TLC), hyperdiffusion chromatography, and the like, and various immunological methods such as fluid or gel precipitation reactions, immunodiffusion, immunoelectrophoresis, radioimmunoassays (RIAs), enzyme-linked immunosorbent assays (ELISA), immunofluorescence assays, tissue array, and the like.

Hybridization techniques are frequently used for detecting nucleic acids and the present invention contemplates all available hybridization techniques, including Southern, Northern and in situ hybridization techniques, dot blot analysis, cDNA arrays. Expression of cytokine mRNAs may be detected, for example, by Northern analysis, or by reverse transcription and amplification by PCR. Also contemplated are nucleic acid detection and quantification methods which employ signal moieties that are conjugated to nucleic acid probes, e.g. by incorporation of radioactively labeled nucleotides. Nucleic acids in a sample can be immobilized on a solid support and hybridized to such probes. The signal moiety can be detected directly, for example by fluorescence. Alternatively, the signal moiety may be detected indirectly by its enzymatic activity, for example in an ELISA or other colorimetric assay.

Hybridization techniques are usually performed by providing a sample of tissue or cells, contacting the sample with a labeled probe, that binds to said nucleic acid molecule, and determining the presence or amount of the probe bound to said nucleic acid molecule, thereby determining the presence or amount of the nucleic acid molecule in said sample.

Methods to quantify the presence and amount of a cytokine protein in a given sample are well known to the person skilled in the art. Briefly, a sample is provided, said sample is contacted with an antibody that immunospecifically binds to a given cytokine and the presence or amount of antibody bound to said cytokine is determined, whereby the presence or amount of cytokines in said sample is determined. Methods to determine the amount and presence of polypeptides comprise, among others, FACS, Western blotting, imnunoprecipitation, ELISA, and RIA. It is advantageous if the antibody used for detection is conjugated to a molecule that enables and contributes to the detection. Suitable molecules comprise biotin, horseradish peroxidase, alkaline phosphatase, fluorescein isothiocyanate (FITC), tetramethylrhodamine isothiocyanate (TRITC), diamidinophenylindol (DAPI) and phycoerythrin.

Thus, the present invention finally embodies a diagnostic kit containing at least one cytokine antagonist being a nucleic acid or a peptide/protein, optionally in combination with suitable buffers, enzymes and other compounds facilitating the detection and quantification of the cytokine in a drug-resistant tumor cell or in a body fluid such as serous effusions (blood), semen, vaginal secretions, saliva, cerebrospinal fluid, pleural and pericardial fluid, peritoneal fluid, synovial fluid and amniotic fluid.

The invention is further illustrated in the following examples:

EXAMPLES

Example 1

Thyroid Cancer Cells are Resistant to Chemotherapy-induced Cell Death

Although clinical trials with single agents or with combinations of chemotherapeutic drugs have produced rare and limited positive response, without increase in median and mean survival time in comparison with the natural history of the disease, some compounds have shown a few beneficial effects in terms of partial response rates and reduction of metastatic tumor expansion.

To investigate the sensitivity of the different histological variants of thyroid epithelial carcinomas to the conventional chemotherapeutic drugs, the viability of freshly purified normal and neoplastic thyrocytes exposed to cisplatin (300 ng/ml), doxorubicin (5 $\mu$M) and taxol (5 $\mu$M was measured, using dosages compatible with the in vivo levels observed during cancer treatment. In line with the modest clinical efficacy reported in clinical trials, primary neoplastic cells derived from all the histological variants of thyroid epithelial carcinomas showed a considerable resistance to chemotherapeutic drugs as compared with normal thyrocytes (FIG. 1). Such resistance persisted for some days and was generally lost after eight to ten days of in vitro culture (results not shown).

Example 2

Thyroid Cancer Cells Express Bcl-2 and Bcl-$x_L$

Refractoriness to chemotherapy of thyroid carcinoma cells may result from the inhibitory action of anti-apoptotic genes. Therefore, the expression of relevant anti-apoptotic proteins, potentially able to protect thyroid cancer cells from the cytotoxic activity of chemotherapeutic drugs was evaluated. Immunohistochemical analysis of PTC, FTC and UTC paraffin embedded sections showed that Bcl-2 and Bcl-$x_L$ were considerably upregulated in thyroid carcinoma cells (FIGS. 2a and b). To determine more accurately the difference between normal and malignant thyrocytes, freshly purified control and neoplastic thyroid cells were lysed and analyzed by immunoblot. As shown in FIGS. 2c and d, Bcl-$x_L$ was weakly expressed in normal cells and four to five fold upregulated in all the histological cancer variants, while Bcl-2 was found about threefold higher in FTC cells and twofold higher in PTC and UTC cells, as compared with normal thyrocytes. Hearts from Bcl-$x_L$ and Bcl-2 transgenic mice were used as positive control. The ability of Bcl-$x_L$ and Bcl-2 overexpression to protect some cell types against the cytotoxic effect of chemotherapeutic drugs suggests a potential role of these anti-apoptotic proteins in thyroid cancer resistance from drug-induced cytotoxicity.

Example 3

Exogenous Bcl-2 and Bcl-$x_L$ Protect Thyrocytes from Cell Death Induced by Chemotherapeutic Agents To prove that Bcl-$x_L$ and Bcl-2 up-regulation protect thyrocytes from apoptosis induced by chemotherapeutic drugs and may be responsible for thyroid cancer cell survival, normal thyrocytes were transduced with a retroviral vector (PINCO) that carried the green fluorescent protein (GFP) as a reporter gene. After infection, thyrocytes transduced with empty vector, Bcl-$x_L$ and Bcl-2 were sorted by flow cytometry and exposed to cisplatinum, doxorubicin and taxol to evaluate the extent of chemotherapy-induced apoptosis. The infections were monitored by immunoblot analysis to confirm the efficiency of gene delivery (FIG. 3a). Thyrocytes transduced with either Bcl-$x_L$ or Bcl-2 were almost completely protected from the cytotoxic effects of chemotherapeutic agents (FIG. 3b and c), indicating that overexpression of any of the two genes was sufficient to prevent thyroid cancer cell destruction. Thus, Bcl-$x_L$ and Bcl-2 represent likely candidates for mediating refractoriness of thyroid cancer cells to chemotherapy.

Example 4

Autocrine Production of IL-4 and IL-10 in Thyroid Cancer Cells

To investigate whether the tumor microenviromnent can influence thyroid cancer cell phenotype and function, the presence of those cytokines previously found to modulate thyrocyte susceptibility to apoptosis was next evaluated. The presence of Th1 and Th2 cytokines in the neoplastic thyroid gland was investigated by immunohistochemistry on paraffin embedded sections of thyroid carcinomas and by immunocytochemistry and immunoblot analysis on freshly isolated thyroid carcinoma cells. All the histological variants analyzed by immunohistochemistry, exhibited a high reactivity for IL-4 and IL-10, as compared with normal tissues, while IFN-γ was barely detectable (FIG. 4a). Interestingly, the reactivity against Th2 cytokines localized in thyroid follicles, suggesting that neoplastic thyroid cells were the source of production for both IL-4 and IL-10 (FIG. 4a). To rule out the possibility that these cytokines were released by infiltrating T cells, freshly purified thyroid cancer cells were analyzed by immunocytochemistry and immunoblot for expression of Th1 and Th2 cytokines. As observed in the immunohistochemistry experiments, purified thyroid cancer cells showed intense reactivity for both IL-4 and IL-10, while no expression of IFN-γ was detectable (FIGS. 4b and c). Twenty nanograms of recombinant human IL-4, IL-10 and IFN-γ were used as positive controls for the immunoblot analysis. The comparison between positive controls and cancer samples indicated that malignant thyroid cells produce considerable amounts of those Th2 cytokines that have shown anti-apoptotic activity on thyroid follicular cells.

Example 5

IL-4 and IL-10 Protect Thyrocytes from Cell Death Induced by Chemotherapeutic Agents It was next investigated whether IL-4 and IL-10 can modulate the sensitivity to chemotherapy-induced apoptosis and the expression of anti-apoptotic proteins in thyroid cells. Interestingly, both IL-4 and IL-10 drastically prevented death of normal thyrocytes exposed to cisplatinum, doxorubicin and taxol (FIG. 5a), suggesting that autocrine production of these cytokines in thyroid cancer cells is responsible for refractoriness to chemotherapy. Furthermore, both IL-4 and IL-10 upregulated Bcl-$x_L$ and Bcl-2 after 48 hours of culture (FIG. 5b), while IFN-γ was not effective. Thus, it is likely that increased expression of anti-apoptotic proteins and subsequent protection of tumor cells from chemotherapy are mediated by the autocrine release of IL-4 and IL-10.

Example 6

Blocking Autocrine IL-4 and IL-10 Activity Primes Thyroid Cancer Cell for Chemotherapy-mediated Destruction To test whether autocrine IL-4 and/or IL-10 release by thyroid tumors is responsible for upregulation of anti-apoptotic proteins, tumor cells were treated for two days with neutralizing Abs specific for IL-4 and/or IL-10 and measured Bcl-$x_L$ and Bcl-2 expression. As shown in FIG. 6a, the levels of both proteins dramatically decreased in thyroid tumor cells exposed to neutralizing Abs against IL-4 and IL-10, while the blockade of a single cytokine had a very limited effect. To test whether cytokine-mediated increase in Bcl-$x_L$ and Bcl-2 levels was responsible for thyroid tumor cell resistance to chemotherapy, PTC, FTC and UTC cells were treated for two days with neutralizing anti-IL-4 and anti-IL10 Abs and analyzed for viability and sensitivity to chemotherapeutic drugs. A significant percentage of thyroid tumor cells from all the histological variants underwent spontaneous apoptosis after 48-hour exposure to anti-IL-4 and anti-IL-10 Abs (FIG. 6a), indicating that these cytokines indeed act as survival factors for thyroid cancer cells. Moreover, these cells acquired sensitivity to chemotherapy-induced cytotoxicity and showed massive death after 24-hour treatment with cisplatinum, doxorubicin or taxol (FIG. 6b). Thus, neutralization of IL-4 and IL-10 released by thyroid cancer cells allows their destruction through the use of chemotherapeutic drugs.

Example 7

Down-regulation of Anti-apoptotic Proteins Sensitizes Cells to TRAIL-induced Cell Death To determine the potential of TRAIL-mediated apoptosis in vivo TRAIL-Receptor (IR) expression in normal and thyroid carcinoma cells was documented. To determine the presence of TRAIL-R1, TRAIL-R2, TRAIL-R3 and TRAIL-R4 immunohistochemical stainings of paraffin embedded thyroid tissue sections from patients affected by PTC, FTC and UTC were performed and compared with sections from normal thyroid lobes contralateral to the cancerous lobe in patients with thyroid cancer. It was found that TRAIL-R1-TR4 were strongly expressed in all the papillary tumors analysed and completely absent in follicular and anaplastic tumors (data not shown). To test whether autocrine IL-4 and IL-10 release is responsible for TRAIL-induced apoptosis resistance in all the histological thyroid cancer variants examined carcinoma cells were treated for two days with IL-4 and IL-10-neutralizing antibodies and then tumor cell resistance to TRAIL-induced apoptosis was measured. A significant percentage of tumor cells was apoptotic after 48 hours' exposure to anti-IL-4 and anti-IL-10 Abs, indicating that these cytokines act as survival factors for these cells (data not shown). Thus, downregulation of anti-apoptotic proteins such as FLIP, Bcl-$x_L$ and Bcl-2, through the inhibition of Th2 cytokines, sensitizes these cells to TRAIL-induced cell death.

Example 8

IL-4 Inhibits Chemotherapy- and CD95-induced Apoptosis in Bladder Cancer Cells

A decreased Th1/Th2 ratio has been observed in a wide variety of human cancers, where it has been proposed to correlate with the stage and grade of malignancy. IL-4 released from tumor-associated Th2 lymphocytes has been shown to promote the growth of pulmonary metastatic cancer in mice, suggesting a specific role of this cytokine in influencing tumor cell survival. Therefore, the ability of IL-4 to modulate apoptosis sensitivity of cells derived from different human solid tumors was investigated.

Anticancer treatment using cytotoxic drugs mediates cell death by activating the intracellular apoptotic program. To determine whether IL-4 was able to inhibit apoptosis induced by chemotherapeutic drugs, bladder tumor cells (RT112)

were pretreated for two days with different concentrations of IL-4 and subsequently exposed to camptothecin or etoposide. While a considerable number (~60%) of tumor cells underwent apoptosis in response to chemotherapeutic agents, cells preincubated with IL-4 were significantly protected from drug-induced death (FIG. 7A), suggesting that IL-4 interferes with the apoptotic program activated by anticancer agents in tumor cells. The protective effect of IL-4 was already consistent after 24 hours of pretreatment and remained stable from the second day of treatment unless IL-4 was removed from the culture medium (FIG. 7B and data not shown).

The observation that tumor cells treated with IL-4 display a reduced sensitivity to chemotherapeutic drugs led us to investigate whether this cytokine would influence the expression of apoptosis regulatory genes. Western blot analysis of apoptosis-related proteins was performed on cancer cell lines treated for 48 hours with IL-4 as compared to untreated or IL-2-treated controls. Among the proteins examined, it was found that levels of Bcl-$x_L$ and cFlip/FLAME-1 were increased in tumor cells treated with IL-4, while levels of caspases and other pro- and anti-apoptotic Bcl-2 family members remained unchanged (FIG. 7C-D and data not shown). The increased expression of cFlip/FLAME-1 prompted us to investigate if IL-4 could protect tumor cells from death receptor stimulation. CD95 ligand (CD95L) is one of the major effector molecules of cytotoxic T lymphocytes and NK cells. The CD95 pathway has been demonstrated to be involved in tumor clearance in vivo. CD95 mutation or downinodulation has been found in several tumors, and the development of resistance to CD95-induced cell death has been suggested to contribute to immune evasion of malignant cells. As shown in FIG. 7E, IL-4 treatment was able to significantly inhibit CD95-induced apoptosis in bladder cancer cells, suggesting that IL-4 can negatively affect the immune response against tumors.

Example 9

IL-4 Inhibits Chemotherapy- and CD95-induced Apoptosis in Prostate and Breast Cancer Cells It was hypothesized that the ability of IL-4 to protect bladder cancer cells from chemotherapy and anti-CD95-induced apoptosis could be also displayed by other tumors characterized by the presence of IL-4, such as prostate and breast cancer. Therefore, tumor cell lines derived from prostate (LNCaP) and breast (MDA-MB-231) carcinomas were pretreated for two days with IL-4 and subsequently exposed to those antineoplastic agents that showed the highest cytotoxic activity towards each cell line. Whilst a considerable percentage of prostate and breast tumor cells cultured in medium alone or pretreated with IL-2 underwent apoptosis in response to chemotherapeutic agents, cells preincubated with IL-4 were significantly protected from drug-induced death (FIG. 8A-B). Similarly, IL-4 greatly reduced anti-CD95-induced apoptosis (FIG. 8C), suggesting that the presence of IL-4 in the tumor infiltrate may protect cancer cells from cytotoxic therapy and immune response. Conversely, pretreatment of cells with IL-2 did not exert any protective effect, demonstrating the specificity of IL-4-mediated signals in the inhibition of apoptosis initiated by CD95 in cancer cells. Notably, cells pretreated with IL-4 not only displayed an increased survival to cytotoxic drugs and CD95 stimulation, but regained full proliferative activity when the cytotoxic stimulus was removed (data not shown). Therefore, it appears that IL-4 is able to exert a significant effect on survival and growth of tumor cells, including a faster expansion of cells that survive chemotherapy treatment.

Example 10

IL-4 Upregulates the Expression of Anti-apoptotic Proteins in Prostate and Breast Cancer Cells The observation that prostate and breast tumor cells treated with IL-4 display a reduced sensitivity to death induced by CD95 and chemotherapeutic drugs led us to investigate whether this cytokine would influence the expression of apoptosis regulatory genes. As for bladder tumor cells, it was found that levels of Bcl-$X_L$ and cFlip/FLAME-1 were considerably upregulated following IL-4 treatment in LNCap prostate cancer cells (FIG. 9A), thus providing a possible explanation for IL-4-mediated protection from apoptotic events initiated by chemotherapy and CD95 receptor. Differently, only a modest increase in cFlip/FLAME-1 was not observed in MDA-MB-231 cells, where Bcl-$X_L$ likely represents the primary effector of IL-4-mediated protection from apoptosis (FIG. 9B). Therefore, IL-4-mediated increased survival in bladder, prostate and breast cancer cells is associated with upregulation of anti-apoptotic proteins.

Example 11

Exogenous Expression of Bcl-$X_L$ or cFlip/FLAME-1 Protects Tumor Cells from Drug-induced Apoptosis Anti-apoptotic Bcl-2 family members regulate the release of cytochrome c from mitochondria and have been implicated in apoptosis modulation of tumor cells exposed to chemotherapeutic drugs. Increased expression of cFlip/FLAME-1 has been reported to inhibit CD95-dependent apoptosis of malignant cells, thus resulting in tumor escape from T cell immunity in vivo. To determine whether increased expression of these two anti-apoptotic effectors was able to protect tumor cells from apoptosis induced by chemotherapeutic drugs, RT112, MDA-MB-231 and LNCAP cells were transduced with a retroviral vector containing the cDNA for Bcl-$X_L$ or cFlip/FLAME-1 and the GFP as a reporter gene. Retroviral infection yielded 100% GFP-positive cell populations, which were then analyzed for expression of the transduced genes. By titrating viral supernatant and modulating the number of infection cycles, it was possible to obtain levels of Bcl-$X_L$ and cFlip/FLAME-1 in transduced cells comparable to those of IL-4-treated cells, as shown by immunoblot analysis and densitometry quantification (FIG. 9C-E). Cells were then exposed to chemotherapeutic drugs, and protection from apoptosis exerted by exogenous Bcl-$X_L$ or cFlip/FLAME-1 was evaluated in relation to non-transduced cells pretreated with IL-4 or with the control cytokine IL-2. Whereas control cells were efficiently killed by cytotoxic drugs, exogenous expression of Bcl-$X_L$ protected tumor cells from drug-induced apoptosis at levels similar to those produced by IL-4 (FIG. 10). A partial inhibition of drug-induced death was also observed in cells overexpressing cFlip/FLAME-1 (FIG. 10), possibly reflecting the ability of cFlip/FLAME-1 to activate anti-apoptotic signals through NF-kB or alternatively indicating the involvement of death receptor-mediated events in chemotherapy-induced apoptosis.

Example 12

Exogenous Expression of Bcl-$X_L$ or cFlip/FLAME-1 Protects Tumor Cells from CD95-induced Apoptosis Bcl-$X_L$ and cFlip/FLAME-1 have both been demonstrated to interfere with apoptotic signals initiated at the CD95 receptor, although with different mechanisms. cFlip/FLAME-1 inactivates the CD95 DISC by blocing the activation of caspase-8, whereas overexpression of Bcl-$X_L$ inhibits the mitochondrial apoptotic pathways, which contribute to the execution phase of death receptor signaling. To determine the capacity of Bcl-$X_L$ and cFlip/FLAME-1 to inhibit CD95-induced apoptosis of tumor cells, RT112, MDA-MB-231 and LNCAP cells stably overexpressing Bcl-$X_L$, and RT112 and LNCAP cells overexpressing cFlip/FLAME-1 were stimulated with anti-CD95 agonistic antibodies. Bcl-$X_L$ was able to induce a significant protection of the three cell lines from CD95-mediated death, indicating an important role of mitochondrial events in CD95-mediated apoptosis of these cells (FIG. 10A-C), while cFlip/FLAME-1 efficiently protected LNCaP and RT112 cells from CD95-induced apoptosis at levels comparable to those obtained with IL-4 treatment (FIGS. 10A and B). These results support the hypothesis that the upregulation of Bcl-$X_L$ and cFlip/FLAME-1 induced by IL-4 may contribute to an increased resistance of tumors to apoptosis mediated by chemotherapeutic drugs and by immune system effectors.

Example 13

In vivo Production of IL-4 is Associated with Upregulation of Bcl-$X_L$ and cFlip/FLAME-1 in Bladder and Prostate Cancer To determine the role of IL-4 in tumor cell protection in vivo, bladder, prostate and breast cancer specimens were analyzed by immunohistochemistry in order to detect the presence of IL-4 and the expression of IL-4-induced anti-apoptotic proteins. In line with literature data, normal and neoplastic tissues consistently showed the presence of IL-4 in all the different types of cancer examined, while normal tissues were essentially negative (FIG. 12A-C). Serial section analysis indicated that IL-4 reactivity was associated with the presence of a $CD45^+$ immune infiltrate, which likely represents the major source of IL-4 production in the different tumors (FIG. 12A-C). Analysis of apoptosis-related proteins showed that bladder, prostate and breast tumors display high reactivity for both Bcl-$X_L$ and cFlip/FLAME-1, whose expression in normal tissues was extremely low or undetectable (FIG. 13A). As expected, the three types of tumor expressed the IL-4 receptor, which was also present in normal tissues (FIG. 13A). Moreover, the levels of Bcl-$X_L$ and cFlip/FLAME-1 observed in vivo were compared with those of cells lines whose exogenous expression of either Bcl-$X_L$ or cFlip/FLAME-1 conferred protection from chemotherapeutic drugs and anti-CD95. The expression of both Bcl-$X_L$ and cFlip/FLAME-1 was similar or even higher in bladder and prostate cancer as compared with the corresponding cell lines carrying the exogenous gene (FIG. 13B and C), while the in vivo expression of Bcl-$X_L$ in breast cancer was slightly lower than that found in transduced MDA-MB-231 (FIG. 13D). Thus, in vivo production of IL-4 in bladder and prostate cancer is associated with high expression of Bcl-$X_L$ and cFlip/FLAME-1, which protect cancer cells from chemotherapy and CD95-mediated apoptosis.

Example 14

In vivo Production of IL-4 Protects Breast Cancer Cells from Chemotherapy

To confirm that IL-4-induced upregulation of Bcl-$X_L$ is able to protect epithelial breast cells from apoptosis, freshly isolated normal breast epithelial cells were exposed to IL-4 and analyzed Bcl-$X_L$ expression and sensitivity to a panel of chemotherapeutic drugs commonly used to treat breast cancer. IL-4 treatment of normal breast epithelial cells considerably increased the expression of Bcl-$X_L$, which reached levels slightly lower than those observed in freshly isolated neoplastic cells (FIG. 14A). Accordingly, IL-4 significantly protected normal breast epithelial cells from apoptosis induced by cisplatin, doxorubicin and taxol (FIG. 14B). To confirm that in vivo exposure to IL-4 is responsible for high Bcl-$X_L$ expression and resistance to chemotherapy in breast cancer, Bcl-$X_L$ expression and sensitivity to apoptosis of primary breast carcinoma cells cultivated in the presence or absence of IL-4 was measured Freshly isolated breast cancer cells expressed high levels of Bcl-$X_L$ and were scarcely sensitive to chemotherapeutic drugs (FIGS. 14C and D). However, after 6 days of in vitro culture in the absence of IL-4, breast cancer cells downregulated Bcl-$X_L$ and became sensitive to chemotherapy-induced apoptosis, while in the presence of IL-4 they maintained high Bcl-$X_L$ levels and low sensitivity to chemotherapeutic drugs (FIGS. 14C and D). Thus, in vivo IL-4 production promotes the survival of breast cancer cells.

Materials and Methods (Referring to Examples 1 to 7 and FIGS. 1 to 6)

Specimens. Thyroid tissues affected by eight PTC (aged 28±5), eight FTC (aged 44±3) and four UTC (aged 65±4.5), were obtained at the time of thyroidectomy. Normal thyroid specimens were obtained from the uninvolved, controlateral lobes of thyroid glands with tumours. Histological diagnosis was based on the identification of papillary elements, on the behavioural characteristics of carcinoma cells (vascular and capsular invasion) and nuclear atypia (shape and chromatin pattern). Transgenic mouse hearts expressing human Bcl-2 and Bcl-$x_L$, provided by G. L. Condorelli (Thomas Jefferson University, Philadelphia, Pa.), were used as positive controls.

Thyroid cell purification and culture. Thyroid tissues from normal, PTC, FTC and UTC were digested for 2 hours with collagenase (1.5 mg/ml) (Gibco BRL, Grand Island, N.Y.) and hyaluronidase (20 µg/ml) (Sigma Chemical Co., St. Louis, Mo.) in DMEM. Thyrocytes were purified from the digested tissues by hematopoietic cell depletion with anti-CD45-coupled beads (Dynal, Wirral Merseyside, U.K.) and 12 hours of flask adherence, which allowed removal of other cells. After additional 12 hours of culture, thyroid cells were allowed to grow in monolayer for the immunocytochemistry or detached with trypsin+EDTA following exposure to cytokines or chemotherapeutic agents for functional and protein analyses. Thyrocytes were cultured in standard DMEM with 10% heat-inactivated FBS (Hyclone Laboratories, Logan, UK) in the presence or absence of human recombinant IL-4 (20 ng/ml), IL-10 (40 ng/ml) or IFN-γ (1000 IU/ml) (uroclone, Paignton, UK) and cisplatin (300 ng/ml), doxorubicin (5 µM) and taxol (5 µM) (Sigma) or TRAIL (Alexis, San Diego, USA). For the IL-4 and IL-10 neutralization, thyroid cancer cells were pretreated, for 48 hours, with anti-human IL-4 and IL-10 neutralizing antibodies (1 µg/ml) (R&D systems, MN, USA).

Cell death quantitation. Apoptotic events of neoplastic thyrocytes were evaluated by DNA staining and flow cytometry analysis. Thyroid cell pellets were resuspended in hypotonic fluoroclrome solution containing propidium iodide (50 µg/ml), in 0.1% sodium citrate and 0.1% Triton X-100. The percentage of hypodiploid nuclei was evaluated as previously described. Alternatively, freshly purified thyrocytes were plated in 96-bottomed plates in triplicate at 15,000 cells/well and cultured. The number of viable cells was detected by CellTiter Aqueous Assay Kit (Promega Corporation, WI, USA) adding 20 µl of solution reagent directly to culture wells, incubating for 1 hours at 37° C. and recording absorbance at 490 nm.

Immunostaining procedure. Immunohistochemical stainings were performed on paraffin embedded thyroid sections 5 µm in thickness. Deparaffinised sections were pre-treated with 3% hydrogen peroxide fro 10 min at room temperature to inhibit endogenous peroxidase. Then slides were incubated for 10 min with Tris Bufferd Saline (TBS) containing 3% bovine serum albumin (BSA) to block the unspecific staining. Following elimination of excess serum, sections were exposed for 1 hour to specific antibodies against Bcl-$x_L$ (H-5, mouse $IgG_1$, Santa Cruz Biotechnology, Inc., Santa Cruz, Calif.), Bcl-2 (124, mouse IgG1, Dako) IL-4 (B-S4 mouse IgG1, Caltag Laboratories, Burlingame, Calif.), IL-10 (B-N10 mouse IgG2a, Caltag), IFN-γ (B27, mouse IgG1, Caltag), TRAIL-R1 to R4 (Alexis, San Diego, USA) or isotype matched controls at appropriate dilutions. Prior to immunostaining for Bcl-2 and Bcl-xl, dewaxed sections were treated for 10 min in microwave oven in 0.1 M citrate buffer. After two washes in TBS, sections were treated with biotinylated anti-rabbit or anti-mouse imnuunoglobulins, washed in TBS and 20 incubated with streptavidin peroxidase (Dako LSAB 2 Kit, Dako Corporation Carpinteria CA, USA). Staining was detected using 3-amino-9-ethylcarbazole (AEC) as a colorimetric substrate. Counterstaining of tissue sections was performed using aqueous hematoxylin.

Protein isolation and Western Blotting. Cell pellets were resuspended in ice-cold NP-40 lysis buffer (50 mM Tris-HCl, pH 7.5, 150 mM NaCl, 1 mM EGTA, 1% NP-40) containing 1 mM PMSF, leupeptin (1 µg/ml), pepstatin (1 µg/ml) and aprotirni (1 µg/ml). Each lysate (30 µg) was fractioned on 12% SDS-polyacrylamide gels and blotted on nitrocellulose (Hybond, Amersham, Little Chalfont Buckinghamshire England, UK). Membrane was blocked for 1 h with nonfat dry milk in TBS containing 0.05% Tween 20 and successively incubated for 2 h with Abs specific to actin (Ab-1, mouse IgM, Calbiochem, Darmstadt, Germany), Bcl-2 (124, mouse IgG1, Upstate Biotechnology Inc.), Bcl-$x_L$ (H-5, mouse IgGl, Santa Cniz Biotechnology), IL-4 (3007.11, mouse IgG1, R&D Systems, Inc., Minneapolis, USA), IL-10 (23738.111, mouse IgG2b, R&D Systems), IFN-γ (25718.111, mouse IgG2a, R&D Systems). After washing, the blots were incubated for 1 hour with HRP-conjugated anti-mouse Abs (Amersham) and visualized using an enhanced chemiluminescence detection system (SuperSignal West Dura Extended duration Sustrate, Pierce, Ill., USA). rhIL-4, rhIL-10 and rhIFN-γ (Euroclone) were used as positive control.

Production of retroviral particles and infection of thyrocytes. Bcl-2 and Bcl-$x_L$ cDNAs were cloned in PINCO vector. The amphotropic Phoenix packaging cell line was transiently transfected with PINCO using the calcium-phosphate/chloroquine method. Infection was performed by culturing $5 \times 10^5$ thyrocytes in 1 ml of 0.45 mM filtered supernatant containing viral particles. Then, cells were centrifuged for 45 min at 1800 rpm and placed back in the $CO_2$ incubator for 2 hours. Three infection cycles were performed before the thyrocytes were placed back in supplemented medium. Sorted and enriched positive cells were plated and exposed to cisplatinum, doxorubicin and taxol for evaluation of cell death.

Materials and Methods (Referring to Examples 8 to 14 and FIGS. 7 to 14)

Cell Culture and Reagents

Human LNCAP prostate cancer cell line and human MDA-MB-231 breast cancer cell line were obtained from the American Type Culture Collection (ATCC, Manassas, Va.). Human RT112 bladder carcinoma cell line was kindly provided by Dr. M. Cippitelli (Regina Elena Cancer Institute, Rome, Italy). Cells were grown in RPMI 1640 (Life Technologies Inc., Grand Island, N.Y.) containing 10% heat inactivated fetal bovine serum supplemented with L-Glutamine 2 mM and 100 units/ml Penicillin-Streptomycin. Cells were kept in 5% $CO_2$ atmosphere and routinely passaged when 80-85% confluent. Human recombinant IL-2 and IL-4 were purchased from PeproTech Inc. (Rocky Hill, N.J.). Camptothecin, cisplatin, daunorubicine, etoposide and vincristine were purchased from Sigma-Aldrich Inc. (Sain Louis, Mo.) and resuspended in DMSO (cisplatin, camptothecin and etoposide) or in $H_2O$ (daunorubicine and vincristine). Anti-CD95 agonistic antibody (clone CH11) was purchased from Upstate Biotechnology (Lake Placid, N.Y.). Monoclonal antibody anti-Bcl-$X_L$ (H5, mouse) was from Santa Cruz (Santa Cruz, Calif.), antibody anti-cFlip/FLAME-1 (NF6, mouse) was kindly provided by Dr. P.H. Krammer (German Cancer Reseach Center, Heidelberg, Germany). Antibody anti β-actin (goat) was purchased from Oncogene (Boston, Mass.):

Normal and cancer tissues from breast, prostate and bladder specimens were digested for 3 hours with collagenase (1.8 mg/ml) (Gibco BRL, Grand Island, N.Y.) and hyaluronidase (25 µg/ml) (Sigma Chemical Co., St. Louis, Mo.) in DMEM. After 12 hours of culture, normal and cancer cells were detached with trypsin+EDTA following exposure to cytokines or chemotherapeutic agents for functional and protein analyses. Cells were cultured in standard DMEM with 10% heat-inactivated FBS (Hyclone Laboratories, Logan, UK) in the presence or absence of human recombinant cytokines.

Cell Viability Assay

Cell viability was determined using the CellTiter 96® $AQ_{ueous}$ One Solution Cell Proliferation Assay (Promega, Madison, Wis.), according to the manufacturer's instructions. The assay is based on reduction of 3-(4,5-dimethylthiazol-2-yl)-5-(3-carboxymethoxyphenyl)-2-(4-sulfophenyl)-2H-tetrazolium, inner salt (MTS) to a colored formazan product that is measured spectrophotometrically. Cells were seeded in 96-well tissue culture plates and incubated at 37° C. in a 5% $CO_2$ incubator overnight. The next day IL-2 or IL-4 were added at a concentration of 20 ng/ml. After two days cells were treated for 10 hours with chemotherapeutic drugs or anti-CD95, then 20 µl of MTS were added to each well. After 3 hours of incubation at 37° C. with the MTS reagent, the plates were read on a Multilabel Counter (Victor2, Wallac, Perkin-Ehmer Inc., Norwalk, Conn.) and dye absorbance was measured at 490 nm.

Immunostaining procedure. Immunohistochemical analyses were performed on 7 µm thick paraffin embedded sections. Deparaffinized sections were treated for 10 min. in microwave oven in 0.1 M citrate buffer. Following elimination of excess serum, sections were exposed for 1 hour to specific antibodies against Bcl-$x_L$ (H-5, mouse $IgG_1$, Santa Cruz Biotechnology, Inc., Santa Cruz, Calif.), CD45RO (UCHL1, mouse IgG2a, Dako Corporation Carpintera CA, USA) IL-4 (B-S4 mouse $IgG_1$, Caltag Laboratories, Burlingame, Calif.), cFLIP (rabbit polyclonal IgG, Upstate Biotechnology, Lake Placid, N.Y.), IL-4R (C-20, rabbit polyclonal IgG, Santa Cruz, Calif.) or isotype matched controls at appropriate dilutions. After two washes in TBS, sections were treated with biotinylated anti-rabbit or anti-mouse immunoglobai, washed in TBS and incubated with streptavidin peroxidase (Dako LSAB 2 Kit). Staining was detected using 3-amino-9-ethylcarbazole (AEC) as a colorimetric substrate. Counterstaining of cells and tissue sections was performed using aqueous hematoxylin.

Western Blotting

Cell pellets were washed twice with cold PBS and lysed on ice for 30 minutes with 1% NP40 lysis buffer (20 mM Tris-HCl pH 7.2, 200 mM NaCl, 1% NP40) in the presence of 1 mM phenylmethylsulphonyl fluoride (PMSF) and 2 µg/ml each of aprotinin, leupeptin and pepstatin. Cell debris was removed by centrifugation at 13,000 rpm for 10 minutes at 4° C. Lysate concentration was determined using the Bio-Rad protein assay (Bio-Rad Laboratories, Richmond, Calif.). Aliquots of cell extracts containing 30 µg of total protein were resolved on 10% or 12% SDS-PAGE and transferred to a Hybond-C extra nitrocellulose membrane (Amersham Pharmacia Biotech, Piscataway, N.J.). Filters were blocked for 1 hour at room temperature in 5% nonfat-dry milk dissolved in TBS-T (10 mM Tris-HCl pH 8.0, 150 mM NaCl, and 0.2% Tween 20) and then incubated in 1% BSA/TBS-T containing a dilution of primary antibody (1:200 anti Bcl-$X_L$, 1:10 anti c-Flip and 1:10000 anti β-actin) for 3 hours (Bcl-$X_L$ and β-actin) or overnight (cFlip). After washing in TBS-T buffer, filters were incubated for 45 minutes in 5% nonfat-dry milk dissolved in TBS-T containing a 1:4000 dilution of corresponding peroxidase-conjugated secondary antibody (Amersham). Proteins were visualized with the enhanced chemiluminescence technique (Super Signal West Pico Pierce, Rockford, Ill.).

Production of Retroviral Particles and Infection of Cell Lines cFlip and Bcl-$X_L$ cDNAs were cloned into the PINCO retroviral vector carrying the Green Fluorescent Protein (GFP) as a reporter gene (25). The amphotropic packaging cell line Phoenix was transfected with the PINCO-1/Bcl-$X_L$, PINCO-1/cFlip plasmnids or with the empty vector by standard calciumn-phosphate-chloroquine method. Culture supernatants containing viral particles were collected after 48 hours, filtered (0.45 µm) and added to 3×10$^5$ cells plated on 6-well plates. For one cycle of infection, cells were centriflged at 1800 rpm for 45 minutes at 32° C. and kept in the incubator for 75 minutes.

Cells were subjected to two infection cycles each day for two consecutive days and then placed in standard medium: GFP-positive cells were analyzed by flow cytometry 24 hours after the last infection cycle (FACScan, Becton Dickinson, San Jose, Calif.).

Statistical Analysis

The percentage of apoptotic cells was derived from the percentage of viable cells that was directly calculated from the values of the MTS assay. The percentage of protection from apoptosis was determined as:

$$\% \text{ protection} = 100\% - X$$

X was calculated with the formule:

$$(C1-C2):100=(S1-S2):X$$

where:

C1 is the viability of untreated control cells, C2 is the viability of control cells treated with the apoptotic stimulus, S1 and S2 are the viability of cells preincubated with cytoldnes or transduced with anti-apoptotic genes, untreated (S1) or treated (S2) with the apoptotic stimuli.

Paired t-test was used to analyze the statistical significance of the experimental results. P values less than 0.05 were considered significant. Data are presented as mean values ±one standard deviation of the mean.

Figure 1:
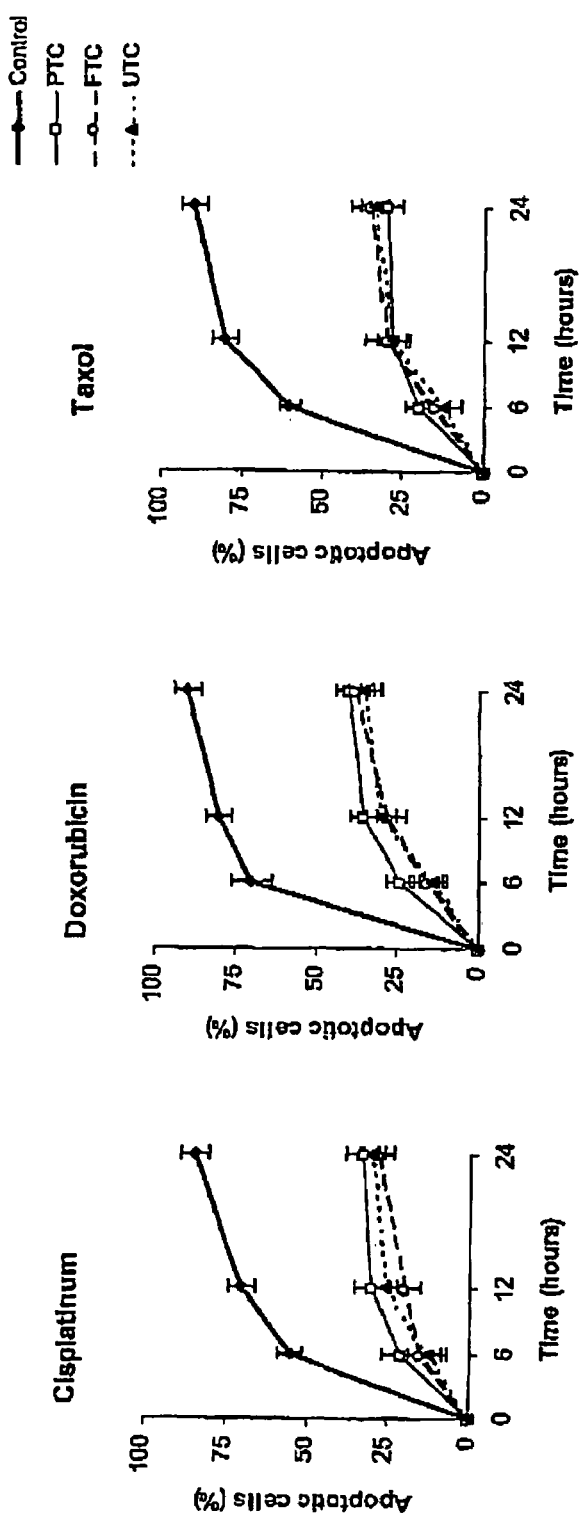
FIG. 1. Resistance to apoptotic cell death induced by chemotherapeutic drugs in thyroid cancer cells. Percentage of apoptotic cells in freshly purified thyrocytes from normal thyroid gland, PTC, FTC and UTC, exposed for 6, 12 and 24 h to cisplatinum (300 ng/ml), doxorubicin (5 µM) and taxol (5 µM). (Data are mean ±s.d. of four independent experiments).

(A) Percentage of viable RT112 bladder carcinoma cells pre-treated for two days with increasing doses of IL-4 (5, 10, 20, 50 and 100 ng/ml) which were maintained also during incubation with chemotherapeutic drugs and exposed to 50 ng/ml camptothecin of 7 µM etoposide. The treatment with 20 ng/ml IL-4 for two days is able to protect cells from chemotherapy-induced apoptosis. The protective effect is maintained at higher concentrations of IL-4 than 20 ng/ml. Cell viability was determined after 24 hours using the MTS assay as described in Materials and Methods and the percentage of protection from cell death was calculated as described in Materials and Methods. The results shown are the mean ±s.d. of four independent experiments.

(B) Time course of RT112 bladder carcinoma cells following exposure with IL-4 are protected from etoposide-induced cell death from day 2 to day 4, until IL-4 is maintained in the culture medium. Cells, pretreated up to 3 days with IL-4 or IL-2, were exposed to 7 µM etoposide for 2 days, washed and placed in fresh medium without cytolines until day 6. When the cytokine is removed by washing the percentage of protection is downmodulated.

(C) Immunoblot analysis of Bcl-$X_L$ and cFlip/FLAME-1 expression levels in RT112. Untreated (0), or treated cells were exposed for two days to 5, 10, 20, 50 or 100 ng/ml IL-4. One representative experiment of two performed is shown.

(D) Immunoblot analysis of Bcl-$X_L$ and cFlip/FLAME-1 expression levels in RT112 untreated (day 0) or treated from day 1 to day 3 with IL-4 and washed and placed in fresh medium without IL-4 from day 3 to day 6.

(E) IL-4 prevents anti CD95-induced apoptosis. Percentage of viable RT112 cells pretreated for two days with IL-4 or IL-2 and kept in the presence of cytokines throughout the experiment. Successively, cells were incubated with 30 ng/ml anti-CD95 agonistic antibody in standard medium. Control cells (−) were stimulated with anti-CD95 in the absence of cytokine pre-treatment. The results shown are the mean ±s.d. of four independent experiments.

*Indicates P<0.05 vs control;  P<0.01 vs IL-2; * P<0.001 vs control or IL-2.

Figure 8:
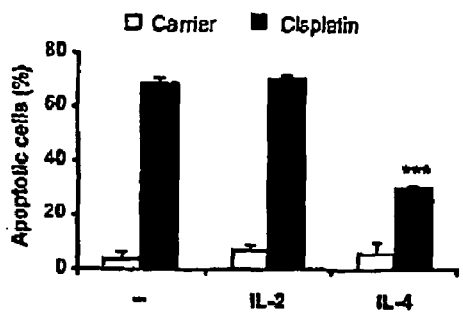
Figure 8:
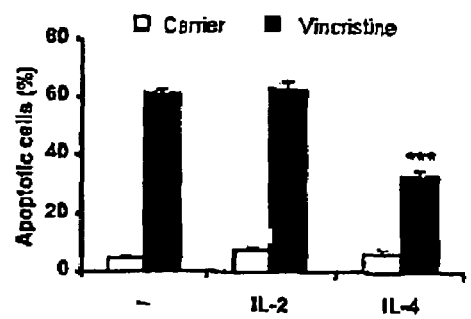
Figure 8:
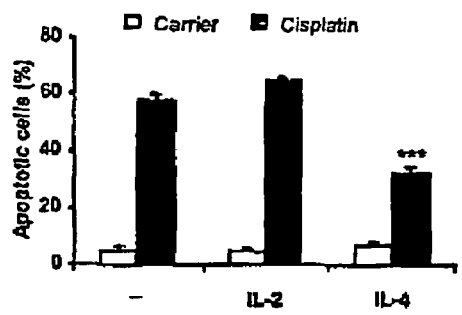
Figure 8:
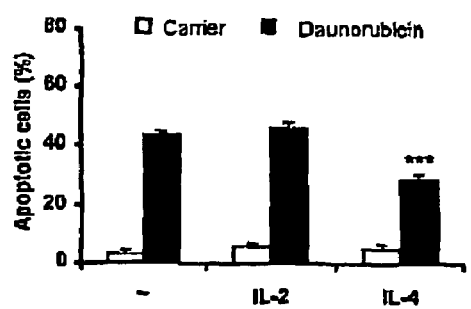
Figure 8:
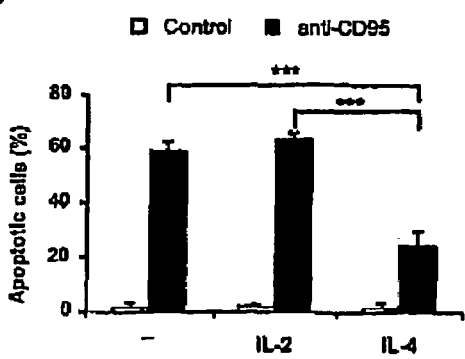
Figure 8:
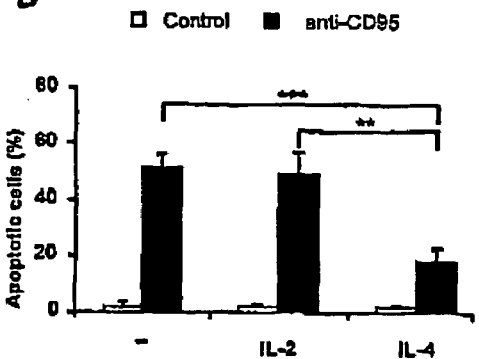

FIG. 8. IL-4 prevents apoptosis induced by chemotherapeutic drugs. Apoptosis percentage of LNCaP prostate cancer cells (A) and MDA-MB-231 breast cancer cells (B) pretreated for two days with IL-4 or IL-2. LNCaP cells were treated with 300 ng/ml cisplatin (left) or 1 µM vincristine (right) and MDA-MB-231 cells were treated with 300 ng/ml cisplatin (left) or 5 µM daunorubicin (right). Control cells (−) were stimulated with chemotherapeutic drugs in the absence of cytokine pretreatment The results shown are the mean ±s.d of four independent experiments.

*** Indicates P<0.001 vs control and IL-2.

IL-4 protects carcinoma cells from CD95-induced apoptosis. Apoptosis evaluation of LNCaP (C) and MDA-MB-231 (D) cells in the presence of IL-4 or IL-2 and incubated with 30 ng/ml anti-CD95 agonistic antibody. Control cells (−) were stimulated with anti-CD95 in the absence of cytokine pre-treatment The results shown are the mean ±s.d. of four independent experiments.

*Indicates P<0.05 vs control;  P<0.01 vs IL-2; * P<0.001 vs control or IL-2.

Figure 9:
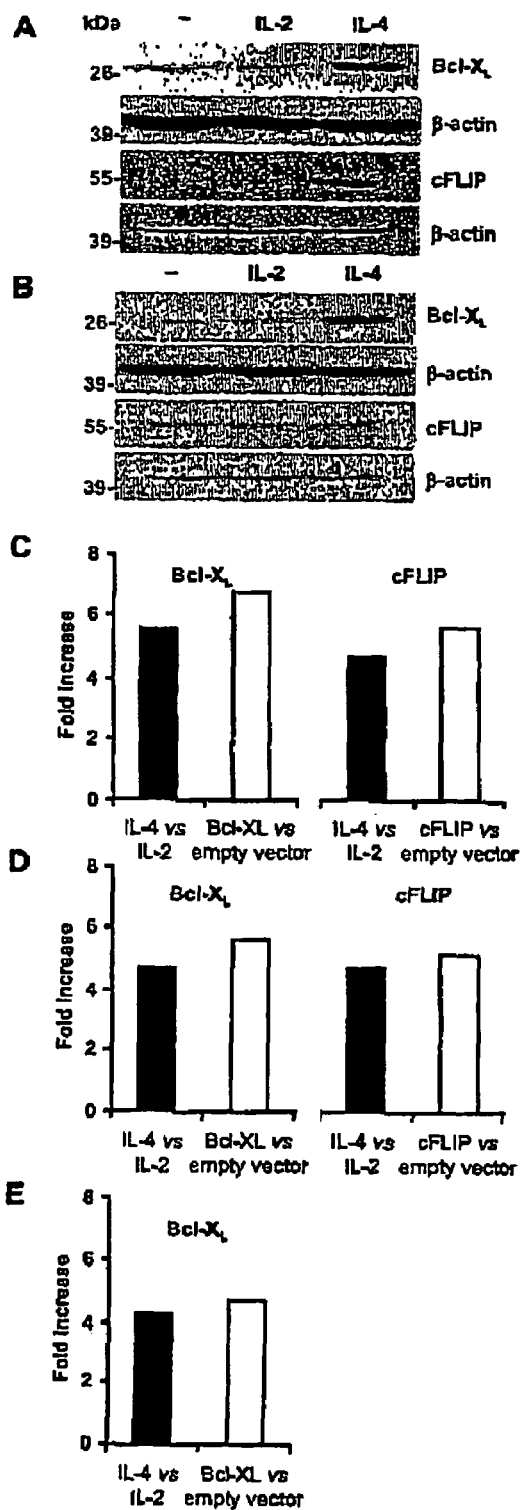

FIG. 9. IL-4 upregulates Bcl-$X_L$ and cFlip/FLAME-1 expression levels. Immunoblot analysis of Bcl-$X_L$ and cFlip/FLAME-1 levels in LNCaP (A) and MDA-MB-231 (B). One representative experiment of four performed is shown.

Comparison of Bcl-$X_L$ and cFlip/FLAME-1 expression in RT112 (C), LNCAP (D) and MDA-MB-231 (E) treated with IL-4 versus the exogenous expression of Bcl-$X_L$ and cFlip/FLAME-1 in retrovirally transduced cancer cells. Data show increase in Bcl-$X_L$ and cFlip/FLAME-1 in IL-4 treated tumor cell lines as compared to IL-2 treated cell lines (filled bars) versus gene-transduced cell lines as compared to empty vector-transduced cell lines (open bars).

Cell populations 100% positive for GFP expression were analyzed 48 hours after the last infection cycle.

Figure 2:
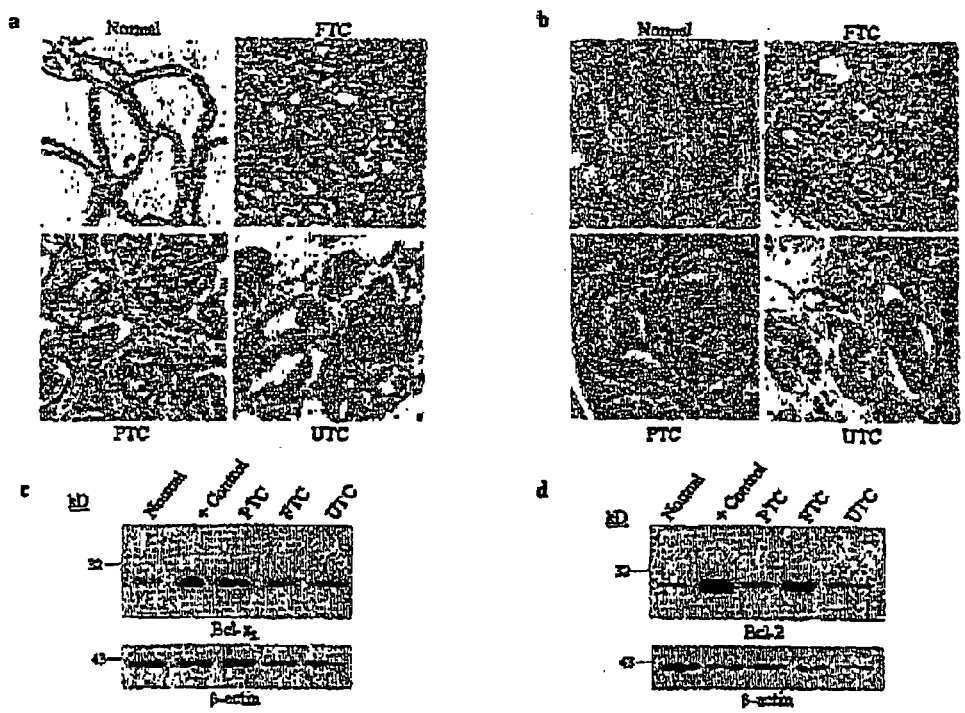
FIG. 2. Anti-apoptotic molecules expression on thyroid cancer. Immunohistochemical analysis of Bcl-$x_L$ (a) and Bcl-2 (b) on paraffin embedded normal thyroid gland, PTC, FTC and UTC sections revealed by AEC (red staining). Immunoblot analysis of Bcl-$x_L$ (c) and Bcl-2 (d) in freshly purified thyrocytes lysates from normal, PTC, FTC and UTC. Bcl-xl and Bcl-2 transgenic hearts were used as positive controls (+control). Loading controls were done by detecting β-actin in the same membrane blot (one representative experiment of four is shown).
Figure 3:
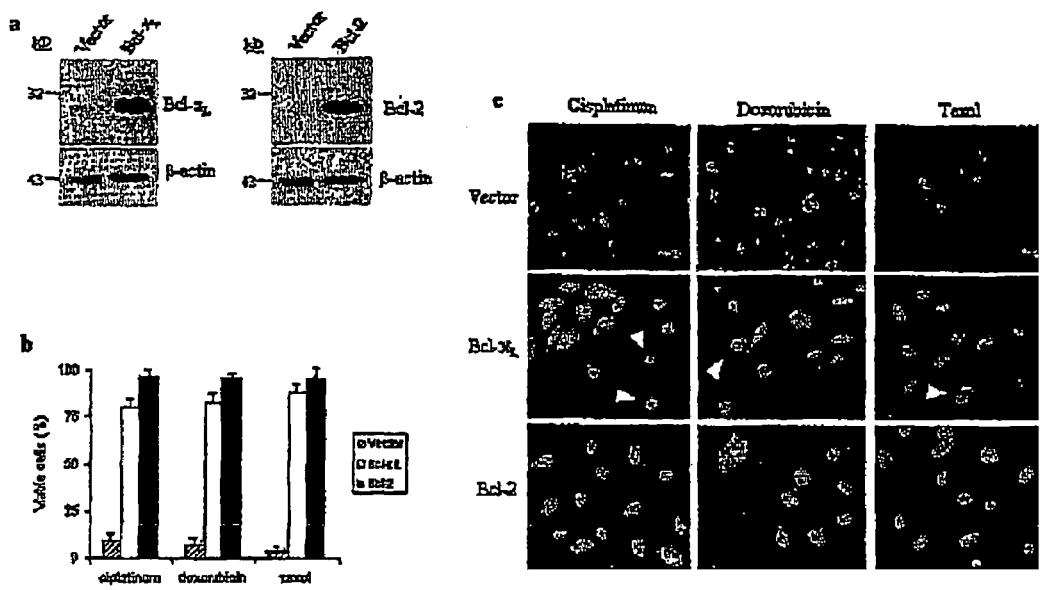
FIG. 3. Protection from chemotherapy-induced cell death in thyrocytes transduced with Bcl-$x_L$ and Bcl-2. Immunoblot analysis of Bcl-$x_L$ (a, left panel) and Bcl-2 (a, right panel) expression on flow cytometry sorted thyrocytes transduced with empty vector (Vector), Bcl-$x_L$ and Bcl-2. Loading control was assessed by β-actin staining. (b) Percentage of apoptosis in normal thyrocytes transduced as in (a) following exposure to chemotherapeutic drugs. (c) GPP-positive cells treated as in (b) followed by staining with ethidium bromide and observed by immunofluorescence microscope. One representative experiment of three performed is shown.
Figure 4A:
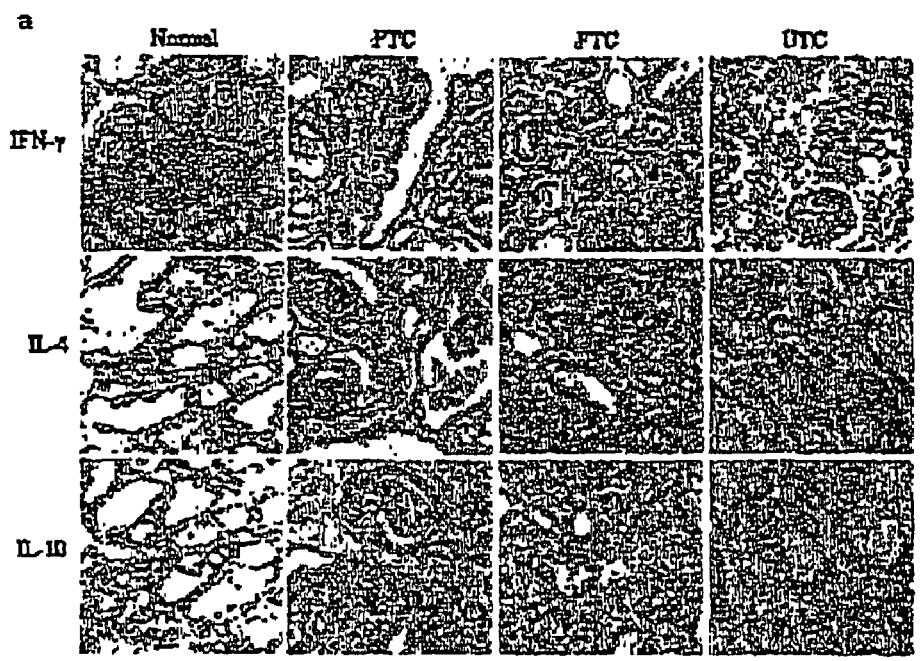
FIG. 4. IL-4 and IL-10 expression on thyroid cancer cells. (a) Immunohistochemical analysis of IL-4, IL-10 and IFN-γ on paraffin embedded normal thyroid gland, PTC, FTC and UTC sections (red staining). (b) Immunostaining for IL-4, IL-10 and IFN-γ of purified thyrocytes from all histological variants of thyroid epithelial carcinoma. (c) Western analysis of IL-4, IL-10 and IFN-γ in freshly purified cancer thyrocytes. rhIL-4, rhIL-10 and rhIFN-γ (20 ng/lane) were used as positive control. These experiments are representative of results from three independent experiments each using cultures from different patient specimens.
Figure 5:
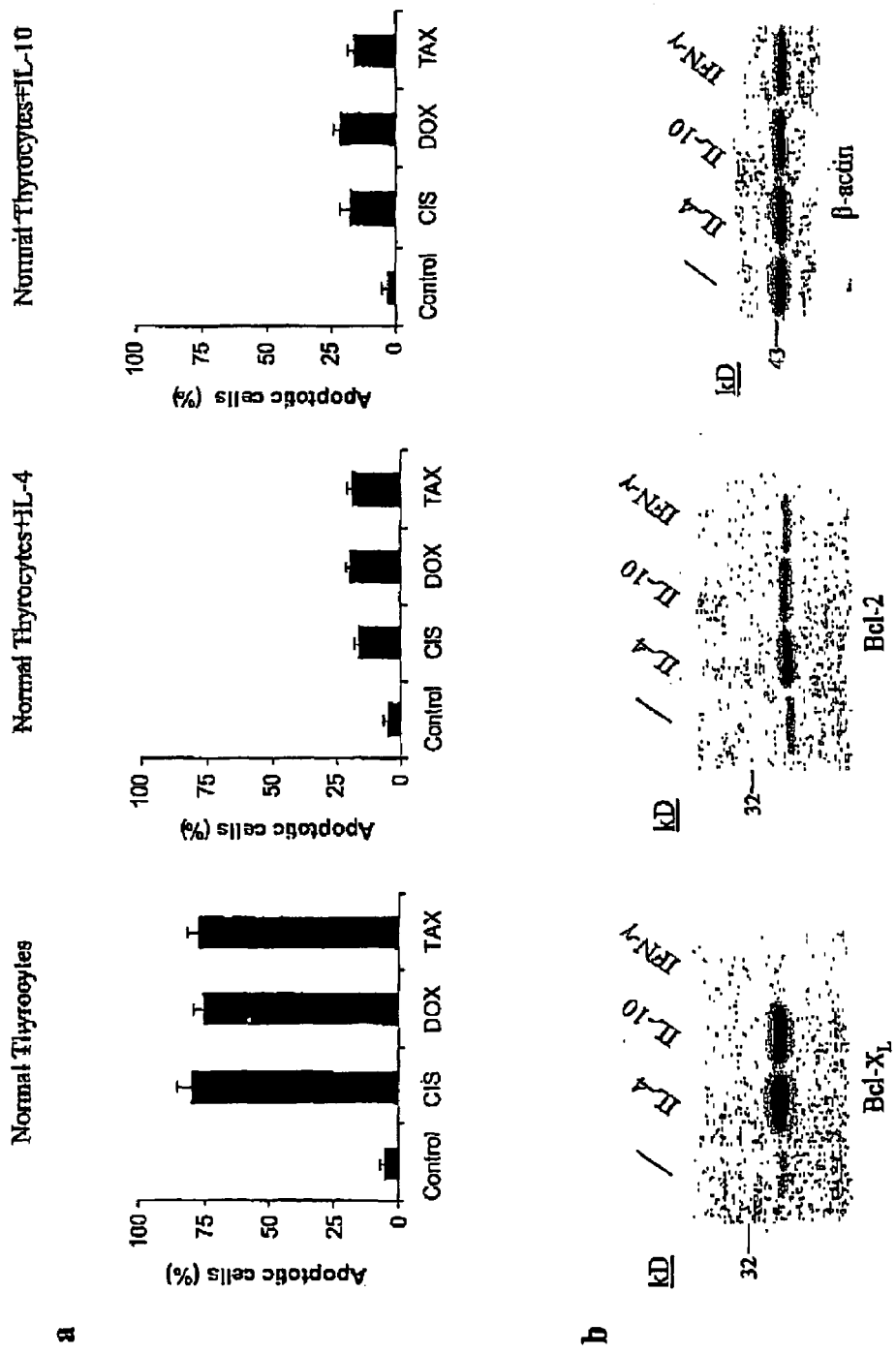
FIG. 5. IL-4 and IL-10 rescue normal thyrocytes from chemotherapy-induced apoptotic cell death. (a) Percentage of apoptotic events of purified normal thyroid cells pre-treated for 48 h with control medium (left panel), rhIL-4 (20 ng/ml) or rhIL-10 (40 ng/ml) and then cultured with cisplatinum, doxorubicin and taxol for 12 additional hours. (b) Immunoblot analysis of normal thyrocytes cultured with IL-4 or IL-10 as in a or rhIFN-γ (1000 IU/ml).
Figure 6A:
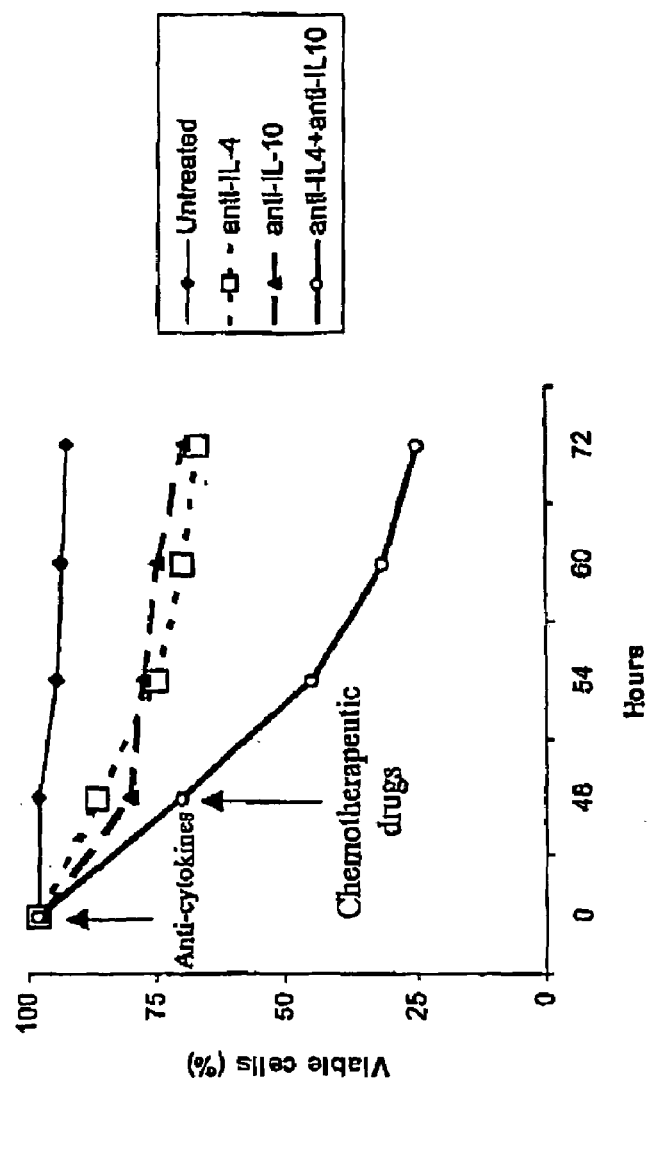
FIG. 6. Neutralizing antibodies against IL-4 and IL-10 sensitize thyroid carcinoma cells to chemotherapy. (a) Kinetics of viable cells on carcinoma thyrocytes cultivated with medium alone or with anti-IL-4 or with anti-IL-10 or with anti-IL-4+anti-IL-10. Percentage of viable purified thyroid carcinoma cells pre-treated for 48 h with control medium, anti-IL-4 (1 µg/ml) or anti-IL-10 (1 µg/ml) or anti-IL-4+anti IL-10 and then cultured with chemotherapeutic drugs for 24 additional hours (right panel). (Mean of one of representative experiment of four is shown). (b) Percentage of viable PTC, FTC and UTC cells pre-treated for 48 h with anti-IL-4+anti IL-10 and then cultured with cisplatinurm, doxorubicin and taxol for 12 and 24 hours.
Figure 6B:
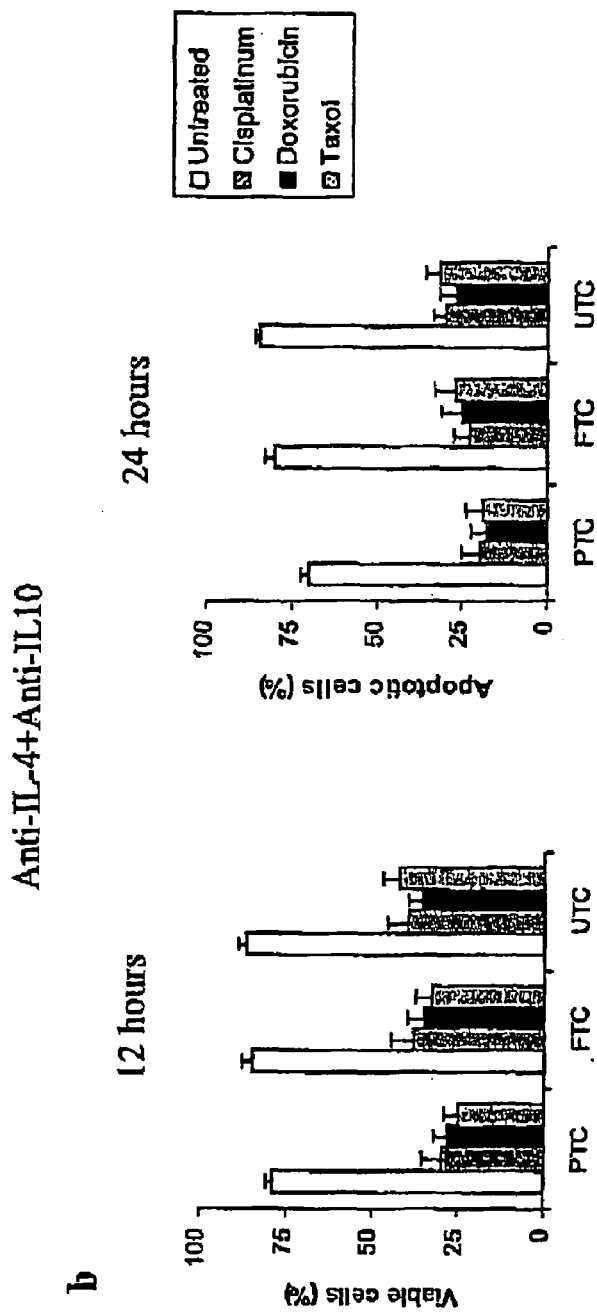
Figure 7:
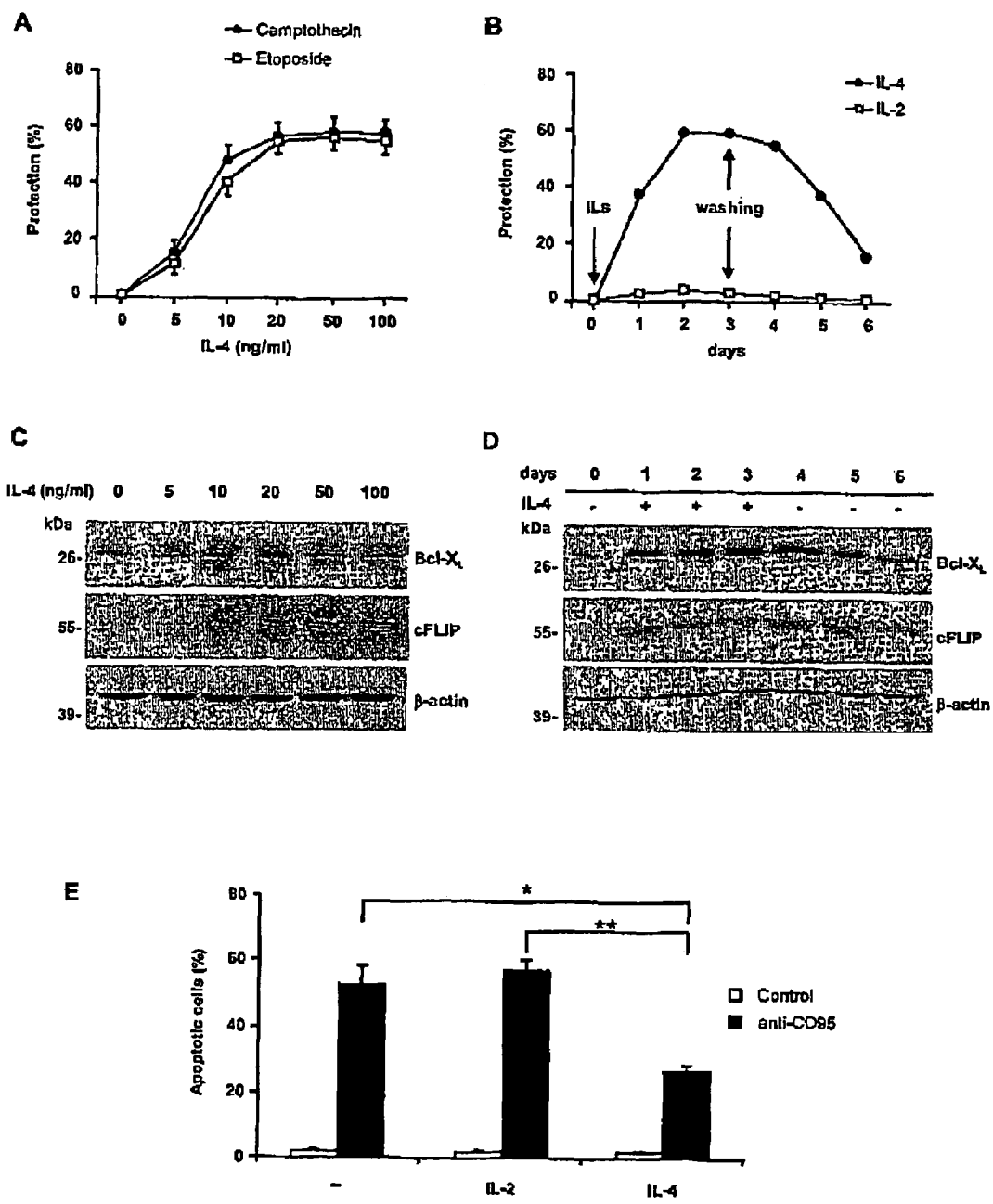
FIG. 7. IL-4 protects RT112 bladder carcinoma cells from chemotherapy- and anti CD95-induced apoptosis.
Figure 10:
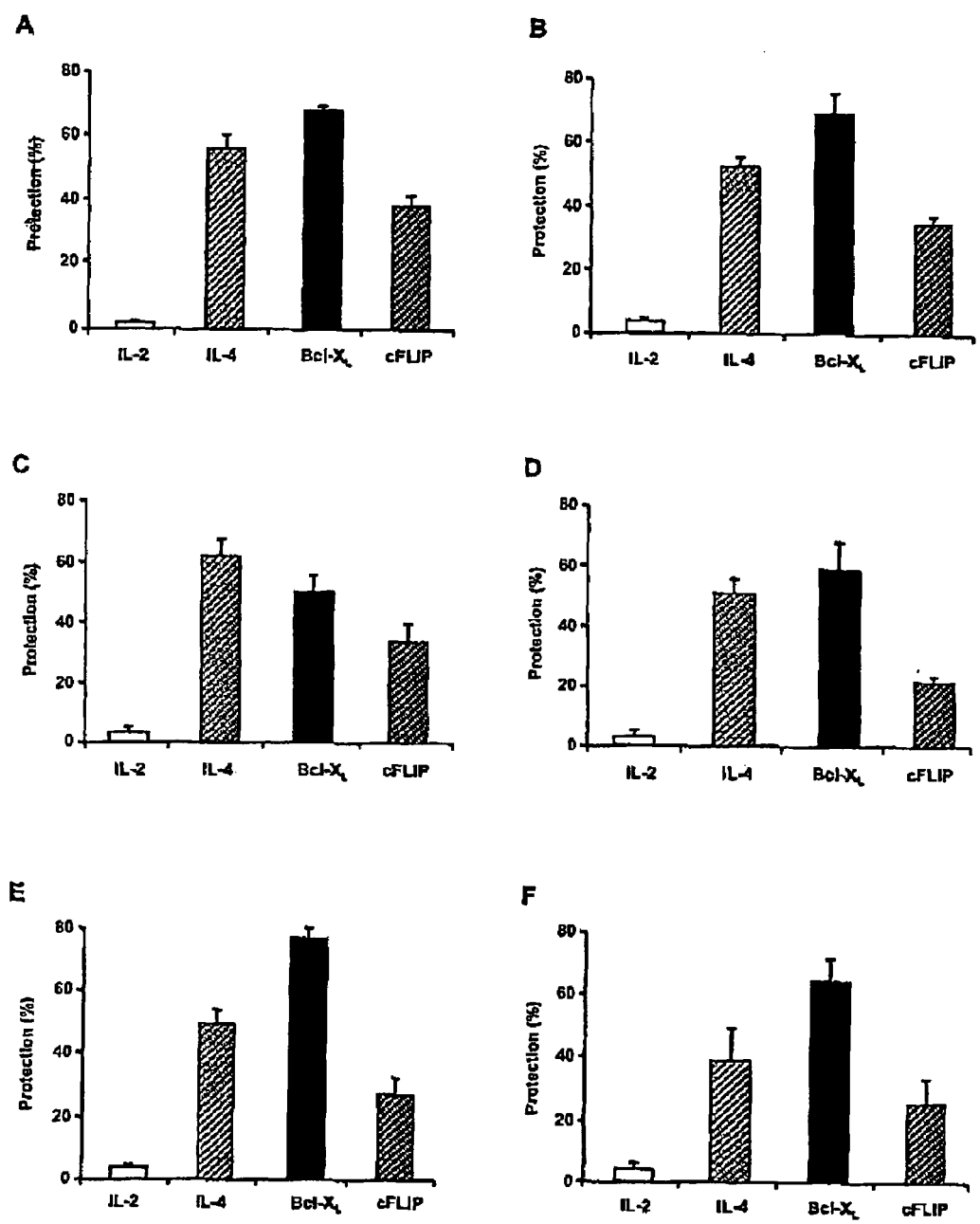

FIG. 10. Exogenous expression of Bcl-$X_L$ or cFlip/FLAME-1 prevents tumor cells chemotherapy-induced apoptosis. Cell lines stably overexpressing Bcl-$X_L$ or cFlip/FLAME-1 were treated with chemotherapeutic drugs as described in FIG. 1 and FIG. 2. RT112 cells were treated with camptothecin (A) or etoposide (B), LNCaP cells treated with cisplatin (C) or vincristine (D), and MDA-MB-231 cells treated with cisplatin (E) or daunorubicin (F). The results shown are the mean ±s.d. of five independent experiments.

Figure 11:
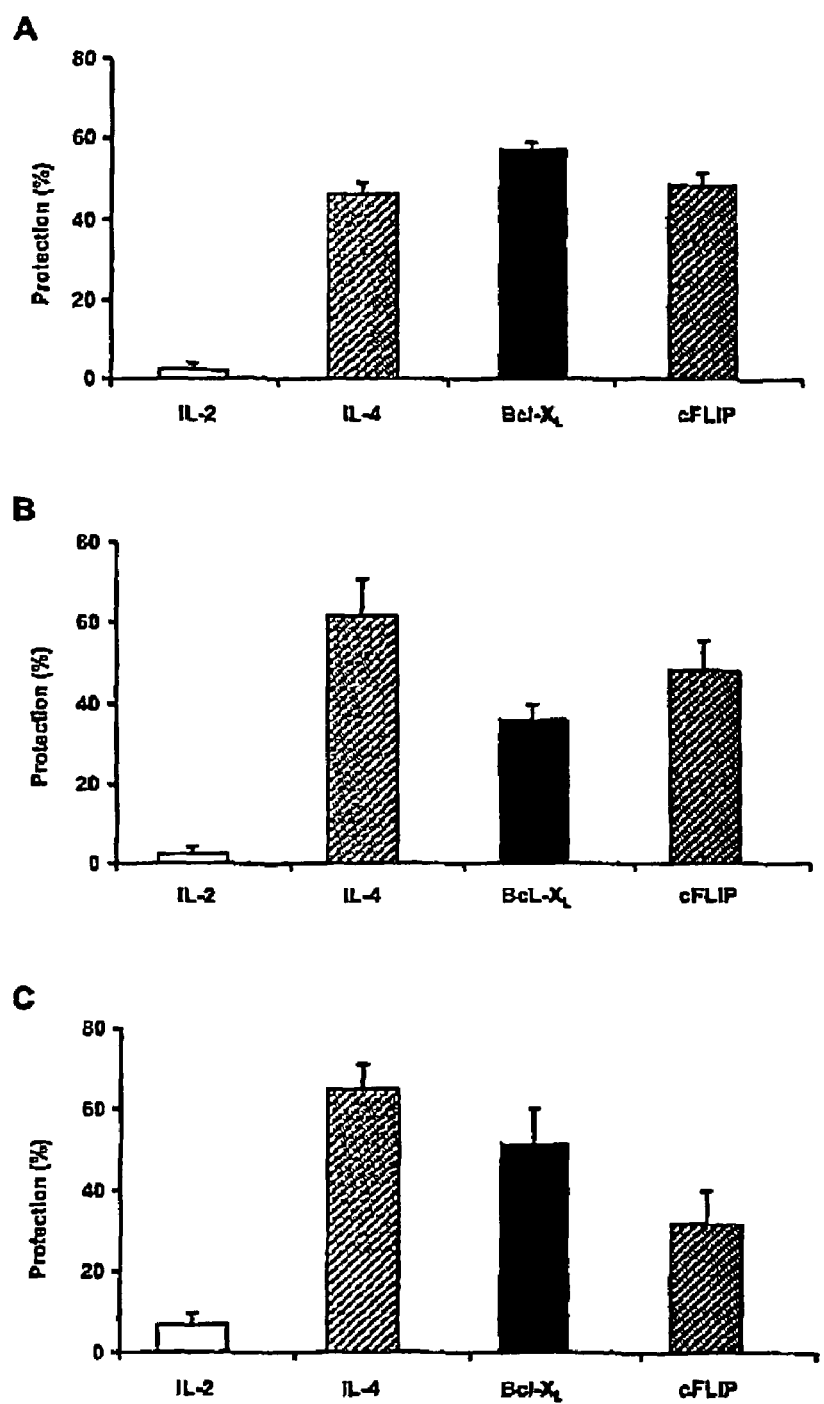

FIG. 11. Exogenous expression of Bcl-$X_L$ or cFlip/FLAME-1 protects tumor cells from anti-CD95-induced apoptosis. RT112 (A), LNCaP (B) and MDA-MB-231 (C) cell lines stably overexpressing Bcl-$X_L$ or cFlip/FLAME-1 treated with anti-CD95 agonistic antibody. The results shown are the mean ±s.d. of five independent experiments.

Figure 12:
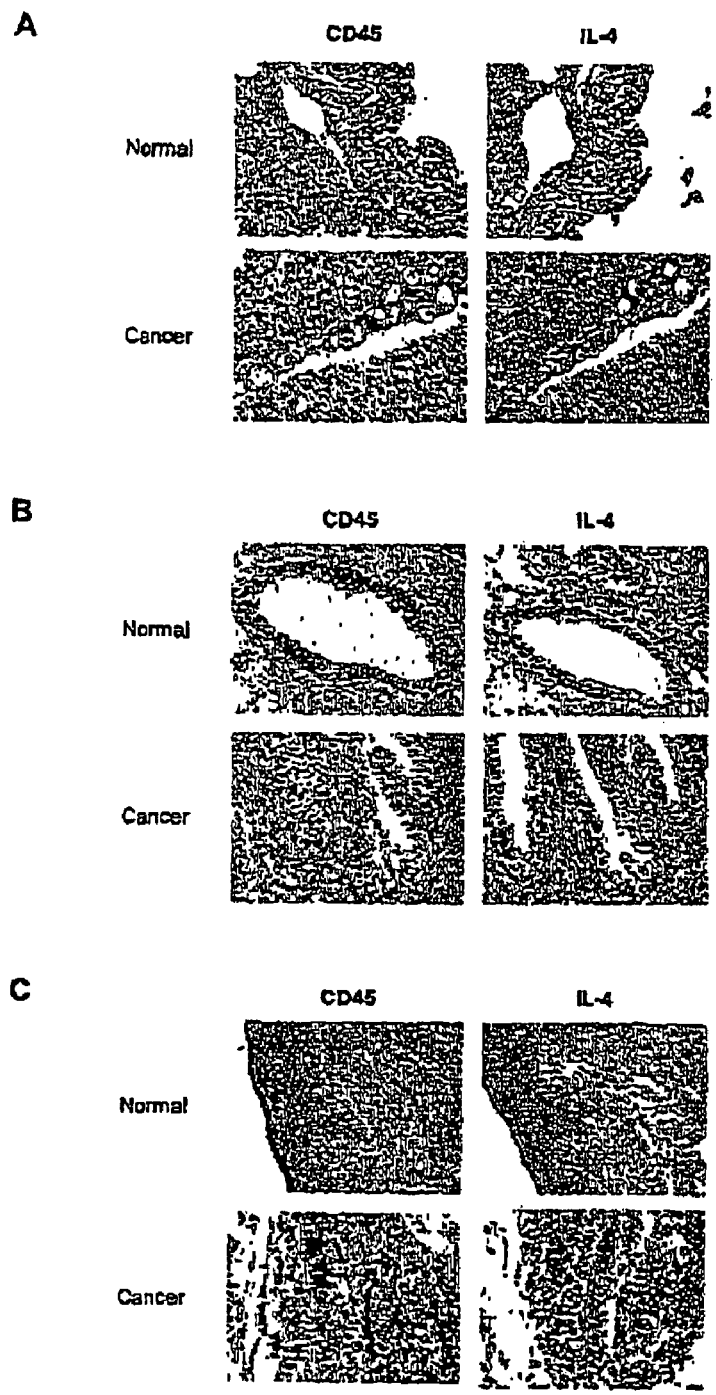

FIG. 12. Immunohistochemical analysis of CD45 and IL-4 on paraffin embedded normal or bladder (A); prostate (B) and breast (C) cancer sections revealed by AEC (red staining).

Figure 13A:
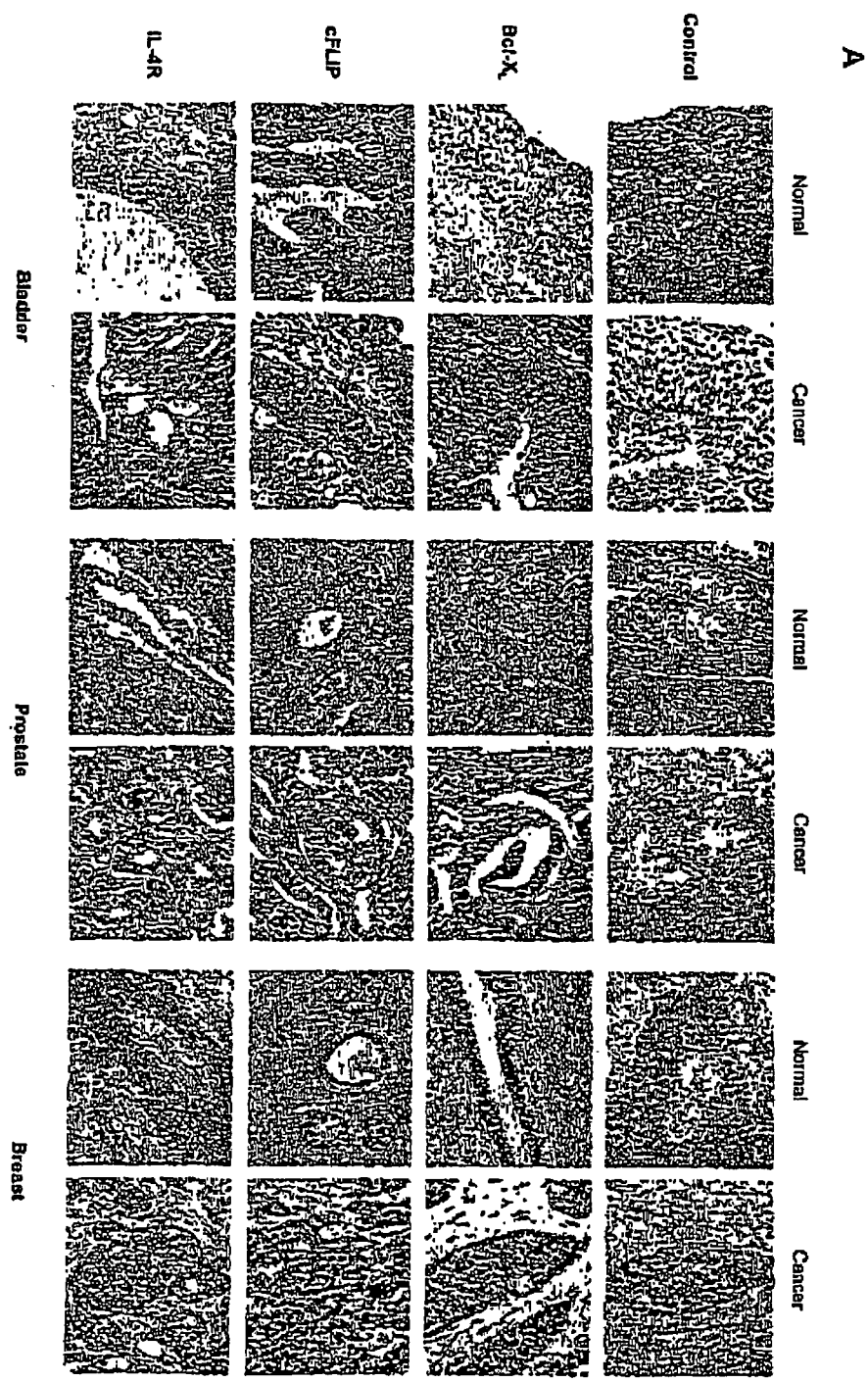

FIG. 13. (A) Immunohistochemical analysis of Bbl-$X_L$, cFlip/FLAME-1 or IL-4R on paraffin sections of normal or bladder, prostate and breast cancer specimens (red color). Exogenous expression of Bcl-$X_L$ and cFlip/FLAME-1 in retrovirally transduced cancer cells, RT112 (B), LNCAP (C) and MDA-MB-231 (D) in comparison with primary tumor cells. Immunoblot analysis of cancer cells transduced with empty vector (vector), with Bcl-$X_L$ or cFlip/FLAME-1 (gene) and primary cancer cells (cancer). One representative experiment of three performed for each cell line is shown.

Figure 14:
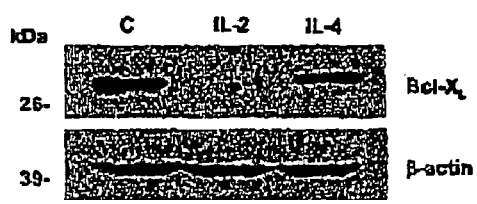
Figure 14:
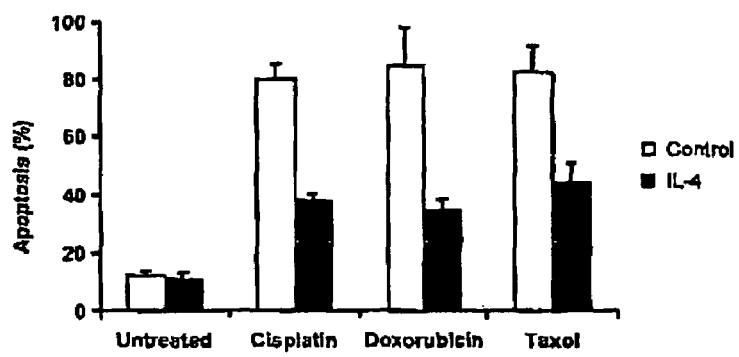
Figure 14:
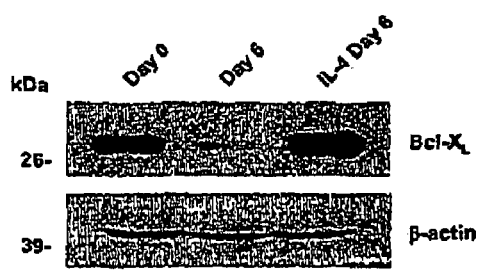
Figure 14:
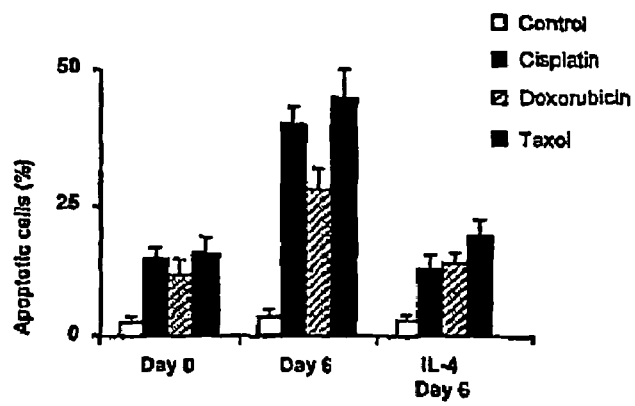

FIG. 14. (A) Immunoblot analysis of Bcl-$X_L$ expression levels in primary cancer cell untreated (C) or treated with IL-2 or IL-4. (B) Percentage of cell death in untreated and IL-4 pretreated cells and exposed to cisplatin, doxorubicin or taxol. Control cells were stimulated with chemotherapeutic drugs in the absence of cytokines pretreatment. (C) Immunoblot analysis of Bcl-$X_L$ in primary cancer cells preincubated for 6 days with or without IL-4. (D) Percentage of apoptotic cell death in primary tumor cells incubated with IL-4 and exposed to cisplatin, doxorubicin and taxol.

The invention claimed is

1. A method for the down-regulation of an anti-apoptotic protein in a non-lymphoid or non-myeloid tumor of a subject, the method comprising the steps of:
   (a) selecting a subject having a non-lymphoid or non-myeloid tumor producing a higher level of a cytokine as compared with normal tissue, wherein the cytokine is selected from the group consisting of interleukin (IL)4, IL-5, IL-10, IL-13, and combinations thereof and having a higher level of an anti-apoptotic protein than a comparable control sample;
   (b) contacting the non-lymphoid or non-lymphoid tumor with a cytokine antagonist;
   wherein the anti-apoptotic protein in the non-lymphoid or non-myeloid tumor is down-regulated; and wherein cells of the non-lymphoid or non-myeloid tumor are sensitized for cell death; and (c) administering to the subject an active compound or radiotherapy.

2. The method according to claim 1, wherein the anti-apoptotic protein is selected from the group consisting of Bcl-2, Bcl-$x_L$, cFLIP, Mcl-1, A1, BOO, NR-13, sentrin, TOSO CPAN, PED, DFF45, NAIP, XIAP, cLAP-1, cLAP-2, ML-IAP, KIAP, BIRC5, TIAP, Apollon, fortilin, and combinations thereof.

3. The method according to claim 1, wherein the cytokine antagonist is selected from the group consisting of a transcriptional regulator of the cytokine/cytokine receptor gene, an antisense nucleic acid molecule that is complementary to a region of the cytokine/cytokine receptor gene, a dsRNA molecule that is complementary to the cytokine/cytokine receptor mRNA, a ribozyme that cleaves the cytokine/cytokine receptor mRNA, a translational regulator of the cytokine/cytokine receptor mRNA, an aptamer which binds to the cytokine and/or cytokine receptor and prevents or disrupts the interaction between the cytokine and its receptor, an antibody that binds to the cytokine/cytokine receptor, a receptor, a fragment or derivative thereof of the cytokine, CD124, CD132, IL-13Rα-2, IL-10Rα, a cytokine trap, and a cytokine mutein.

4. The method according to claim 3, wherein the cytokine antagonist is an antibody that binds to the cytokine/cytokine receptor.

5. The method according to claim 4, wherein the antibody or fragment thereof is an antibody or fragment thereof that binds to IL-4, IL-10, or IL-13, and combinations thereof.

6. The method according to claim 1, wherein the cytokine antagonist is delivered to the proximity of or into, the non-lymphoid or non-myeloid cancer cell.

7. The method according to claim 6, wherein the cytokine antagonist is delivered via a retroviral vector.

8. The method according to claim 1, wherein the active compound is selected from the group consisting of antimetabolite, a DNA-fragmenting agent, a DNA-crosslinking agent, an intercalating agent, a protein synthesis inhibitor, a topoisomerase I poison, a topoisomerase II poison, a microtubule-directed agent, a kinase inhibitor, an investigational agent, a farnesyl transferase inhibitor, a polyphenol, a hormone, a hormone antagonist, a plant-derived cytostatic, an alkaloid, a podophyllotoxin, an alkylant, a cytotoxic antibiotic, a folic acid analog, a purine analog, a pyrimidine analog, a platinum compound, a monoclonal antibody, an antineoplastic agent, an antineoplastic compound derived from an organ, an antineoplastic compound derived from enzyme, an endocrine effecting an antineoplastic compound belonging to hormones, estrogens, gestagens, hypothalamus hormones, an endocrine effecting an antineoplastic compound belonging to hormone antagonists, antiestrogens, antiandrogens, and an endocrine effecting an antineoplastic compound belonging to enzyme inhibitors.

9. The method according to claim 8, wherein the active compound is selected from the group consisting of cytarabine, fludarabine, 5-fluoro-2'-deoxyuiridine, gemcitabine, hydroxyurea, methotrexate, bleomycin, chlorambucil, cisplatin or cisplatinum, cyclophosphamide, nitrogen mustard, adriamycin, mitoxantrone, L-asparaginase, cycloheximide, puromnycin, diphtheria toxin, camptothecin, topotecan, etoposide, teniposide, colcemid, colchicines, paclitaxel, vinblastine, vincristine, flavopiridol, staurosporin, ST1571 (CPG 57148B), UCN-01 (7-hydroxystaurasporine), PS-341, phenylbutyrate, ET-18-OCH$_3$, L-739749, L-744832, quercetin, resveratrol, piceatannol, epigallocatechine gallate, theaflavins, flavanols, procyanidins, betulinic acid, glucocorticoids, fenretinide, tamoxifen, finasteride, LHRH antagonists, vindesine, vinorelbin, nimustine, carmustine, lomustine, estramustrine, melphalam, ifosfamide, trofosfamide, bendamustine, dacarbazine, busulfane, procarbazine, treosulfene, tremozolamide, thiotepa, aclarubicine, daunorubicine, epirubicine, idarubicine, mitomycine, dactinomycine, methotrexate, cladribin, mercaptopurin, tioguanine, cytarabine, fluorouracil, docetaxel, ghioplatin, carboplatin, oxaliplatin, amsacrine, irinotecane, interferon-α, tretinoine, hydroxycarbamide, miltefosine, pentostatine, aldesleukine, trastuzumab, rituximab, pegaspargase, polyestradiol, fosfestriol, ethinylestradiol, medroxyprogesterone, gestonoroncaproat, megestrol, norethisterone, lynestrenol, triptoreline, leuproreline, busereline, gosereline, testolactone, testosterone, toremifen, flutamide, bicalutamide, cyproterane, anastrol, exemestane, letrozol, formestane, and aminoglutethimide.

10. The method of claim 8, wherein the active compound is co-administered with:
(i) a protective selected from the group consisting of calciumfolinat, amifostin, lenograstin molgromostin, filgrastin, and mesna;
(ii) an additive selected from the group consisting of retinolpalmitate, thymus D9, and amilomer; or
(iii) a combination of (i) and (ii).

11. The method according to claim 1, wherein the active compound is a death receptor agonist.

12. The method according to claim 11, wherein the death receptor agonist is a death receptor ligand selected from the group consisting of TNF-α, TNF-β, LT-β, TRAIL, CD95 ligand, TRAMP ligand, DR6 ligand, and fragments and derivatives thereof.

13. The method according to claim 11, wherein the death receptor agonist is an antibody against a death receptor, a derivative, or fragment thereof, selected from the group consisting of anti-CD95 antibody, anti-TRAIL-R1 antibody, anti-TRAIL-R2 antibody, anti-DR6 antibody, anti-TNF-R1 antibody, and anti-TRAMP antibody.

14. The method according to claim 1, wherein the active compound is a negative regulator of an anti-apoptotic protein.

15. The method according to claim 1, wherein the non-lymphoid or non-myeloid tumor is selected from the group consisting of bladder carcinoma, neuroblastoma, intestine carcinoma, rectum carcinoma, colon carcinoma, familiary adenomatous polyposis carcinoma, hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, follicular thyroid carcinoma, anaplastic thyroid carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumor, glioblastoma, astrocytoma, meningioma, medulloblastoma, peripheral neuroectodermal tumor hepatocellular carcinoma, gall bladder carcinoma, bronchial carcinoma, small cell lung carcinoma, non-small cell lung carcinoma, basalioma, teratoma, retinoblastoma, choroids melanoma, seminoma, rhabdornyosarcoma, craniopharyngeoma, osteosarcoma, chondrosarcoma, myosarcome, liposarcoma, fibrosarcoma, Ewing sarcoma, and plasmocytoma.

16. A method for the down-regulation of an anti-apoptotic protein in a non-lymphoid or non-myeloid tumor, the method comprising the steps of:
(a) selecting a subject having a non-lymphoid or non-myeloid tumor producing a higher level of a cytokine as compared with normal tissue, wherein the cytokine is selected from the group consisting of interleukin (IL)-4, IL-5, IL-10, IL-13, and combinations thereof and having a higher level of an anti-apoptotic protein than a comparable control sample; and (b) contacting the non-lymphoid or non-myeloid tumor with a cytokine antagonist selected from the group consisting of a transcriptional regulator of the cytokine/cytokine receptor gene, an antisense nucleic acid molecule that is complementary to a region of the cytokine/cytokine receptor gene, a dsRNA molecule that is complementary to the cytokine/cytokine receptor mRNA, a ribozyme that cleaves the cytokine/cytokine receptor mRNA, a translational regulator of the cytokine/cytokine receptor mRNA, an aptamer which binds to the cytokine and/or cytokine receptor and prevents or disrupts the interaction between the cytokine and its receptor, an antibody or fragment thereof that binds to the cytokine/cytokine receptor, a receptor, a fragment or derivative thereof of the cytokine, CD124, CD132, IL-13Rα-2, IL-10Rα, a cytokine trap, and a cytokine mutein wherein the anti-apoptotic protein in the non-lymphoid or non-myeloid tumor is down-regulated.

17. The method according to claim 16, wherein the cytokine antagonist is delivered to the proximity of or into the non-lymphoid or non-myeloid tumor.

18. The method according to claim 17, wherein the cytokine antagonist is delivered via a retroviral vector.

19. The method according to claim 1, wherein the non-lymphoid or non-myeloid tumor is a colon carcinoma.

20. The method according to claim 1, further comprising the steps of:
(d) detecting the cytokine in a sample obtained from the subject.

21. The method according to claim 20, wherein step (d) comprises detecting a cytokine polypeptide.

22. The method according to claim 20, wherein step (d) comprises detecting a cytokine nucleic acid.

23. The method according to claim 4, wherein the antibody or fragment thereof that binds to the cytokine/cytokine receptor is an anti-IL-4 antibody or an anti-IL-4 receptor antibody or a fragment thereof.

24. The method according to claim 23, wherein the antibody or fragment thereof is an anti-IL-4 receptor antibody or a fragment thereof.

25. The method according to claim 5, wherein the antibody or fragment thereof is a bispecific antibody or fragment thereof.

26. The method according to claim 25, wherein the antibody or fragment thereof is a bispecific antibody or a fragment thereof binding to IL-4 and IL-10.

27. The method according to claim 16, wherein the cytokine antagonist is an antibody or fragment thereof that binds to the cytokine/cytokine receptor.

28. The method according to claim 27, wherein the antibody or fragment that binds to the cytokine/cytokine receptor is an antibody or fragment thereof that binds to IL-4, IL-10, or IL-13, and combinations thereof.

29. The method according to claim 27, wherein the antibody or fragment thereof that binds to the cytokine/cytokine receptor is an anti-IL-4 antibody or an anti-IL-4 receptor antibody or a fragment thereof.

30. The method according to claim 29, wherein the antibody or fragment thereof is an anti-IL-4 receptor antibody or a fragment thereof.

31. The method according to claim 29, wherein the antibody or fragment thereof is a bispecific antibody or fragment thereof.

32. The method according to claim 31, wherein the antibody or fragment thereof is a bispecific antibody or a fragment thereof binding to IL-4 and IL-10.

33. The method according to claim 1, wherein cells of the non-lymphoid or non-myeloid tumor are refractory to administration of the active compound or radiotherapy without administering of the cytokine antagonist.

34. The method according to claim 1, wherein an area of the non-lymphoid or non-myeloid tumor has been surgically removed from the subject.

35. The method according to claim 1, wherein cells of the non-lymphoid or non-myeloid tumor are resistant to an anti-cancer drug or resistant to apoptosis.

36. The method according to claim 1, wherein cells of the non-lymphoid or non-myeloid tumor show a multi-drug resistant phenotype.

37. The method according to claim 1, wherein the cytokine is IL-4.

38. The method according to claim 1, wherein the cytokine is IL-10.

39. The method according to claim 1, wherein the cytokine is IL-13.

40. The method according to claim 2, wherein the anti-apoptotic protein is Bcl-2.

41. The method according to claim 2, wherein the anti-apoptotic protein is $Bcl-x_L$.

42. The method according to claim 2, wherein the anti-apoptotic protein is cFLIP.

43. The method according to claim 3, wherein the cytokine antagonist is a cytokine mutein.

44. The method according to claim 3, wherein the cytokine antagonist is a receptor, a fragment or derivative thereof of the cytokine.

45. The method according to claim 3, wherein the cytokine antagonist is an aptamer which binds to the cytokine and/or cytokine receptor and prevents or disrupts the interaction between the cytokine and its receptor.

46. The method according to claim 8, wherein the active compound is an intercalating agent.

47. The method according to claim 8, wherein the active compound is a microtubule-directed agent.

48. The method according to claim 8, wherein the active compound is a DNA cross-linking agent.

49. The method according to claim 8, wherein the active compound is an antineoplastic agent.

50. The method according to claim 9, wherein the active compound is cisplatin or cisplatinum.

51. The method according to claim 9, wherein the active compound is paclitaxel.

52. The method according to claim 9, wherein the active compound is daunorubicine.

53. The method according to claim 9, wherein the active compound is adriamycin.

54. The method according to claim 14, wherein the anti-apoptotic protein is an IAP.

55. The method according to claim 15, wherein the non-lymphoid or non-myeloid tumor is prostate carcinoma.

56. The method according to claim 15, wherein the non-lymphoid or non-myeloid tumor is breast carcinoma.

57. The method according to claim 15, wherein the non-lymphoid or non-myeloid tumor is medullary thyroid carcinoma, papillary thyroid carcinoma, follicular thyroid carcinoma or anaplastic thyroid carcinoma.

58. The method according to claim 15, wherein the non-lymphoid or non-myeloid minor is colon carcinoma, familiary adenomatous polyposis carcinoma or hereditary non-polyposis colorectal cancer.

59. The method according to claim 15, wherein the non-lymphoid or non-lymphoid tumor is bladder carcinoma.

60. The method according to claim 15, wherein the non-lymphoid or non-myeloid tumor is urinary carcinoma.

61. The method according to claim 15, wherein the non-lymphoid or non-myeloid tumor is pancreatic carcinoma.

62. The method according to claim 16, wherein the cytokine antagonist is a cytokine mutein.

63. The method according to claim 16, wherein the cytokine antagonist is a receptor, a fragment or derivative thereof of the cytokine.

64. The method according to claim 16, wherein the cytokine antagonist is an aptamer which binds to the cytokine and/or cytokine receptor and prevents or disrupts the interaction between the cytokine and its receptor.

* * * * *

UNITED STATES PATENT AND TRADEMARK OFFICE
CERTIFICATE OF CORRECTION

| | | |
|---|---|---|
| PATENT NO. | : 7,645,449 B2 | Page 1 of 3 |
| APPLICATION NO. | : 10/544794 | |
| DATED | : January 12, 2010 | |
| INVENTOR(S) | : Stassi et al. | |

It is certified that error appears in the above-identified patent and that said Letters Patent is hereby corrected as shown below:

In column 1, line 27, please delete "insfficient", and insert --insufficient--.

In column 2, line 4, please delete "drag", and insert --drug--.

In column 2, line 16, please delete "apoptic", and insert --apoptotic--.

In column 2, line 46, please delete "-many", and insert --many--.

In column 2, line 66, please delete "that, e.g.", and insert --that, e.g.--.

In column 4, line 14, please delete "LAPs", and insert --IAPs--.

In column 4, lines 15 and 16, please delete "preventing the ongoing of the apoptosis process", and insert --inhibiting apoptotic processes--.

In column 5, line 17, please delete "cerain", and insert --certain--.

In column 7, line 1, please delete "thereof It", and insert --thereof. It--.

In column 7, line 4, please delete "abispecific", and insert --a bispecific--.

In column 7, line 22, please delete "spiegelbners", and insert --spiegelmers--.

In column 7, line 35, please delete "feasable", and insert --feasible--.

In column 9, line 36, please delete "field If", and insert --field. If--.

In column 10, line 63, please delete "deoxyuiridine", and insert --deoxyuridine--.

In column 11, line 26, please delete "tioguanine", and insert --thioguanine--.

In column 11, line 31, please delete "enyzmes", and insert --enzymes--.

Signed and Sealed this

Twenty-seventh Day of April, 2010

David J. Kappos
*Director of the United States Patent and Trademark Office*

In column 13, line 26, please delete "tong", and insert --tongue--.

In column 13, line 38, please delete "myeolid", and insert --myeloid--.

In column 14, line 9, please delete "insnfficiency", and insert --insufficiency--.

In column 14, line 13, please delete "multifonme", and insert --multiforme--.

In column 14, line 18, please delete "Guiliain-Barré", and insert --Guillain-Barré--.

In column 14, line 19, please delete "Mfller-Fischer", and insert --Miller-Fisher--.

In column 14, line 34, please delete "anmiotic", and insert --amniotic--.

In column 14, line 51, please delete "usefil", and insert --useful--.

In column 14, line 57, please delete "cytolines", and insert --cytokines--.

In column 16, line 8, please delete "(5 µm", and insert --(5 µm)--.

In column 19, line 29, please delete "downinodulation", and insert --down modulation--.

In column 20, line 65, please delete "NF-kB", and insert --NF-κB--.

In column 21, line 9, please delete "blocling", and insert --blocking--.

In column 22, line 12, please insert --was-- between "and" and "analyzed".

In column 22, line 24, please delete "measured Freshly", and insert --measured. Freshly--.

In column 23, line 4, please delete "fluoroclrome", and insert --fluorochrome--.

In column 23, line 12, please delete "37° C. and", and insert --37° C and--.

In column 23, line 17, please delete "fro", and insert --for--.

In column 23, line 19, please delete "Bufferd", and insert --Buffered--.

In column 23, line 24, please delete "Dako) IL-4", and insert --Dako), IL-4--.

In column 23, line 33, please delete "20".

In column 23, line 42, please delete "aprotirni", and insert --aprotinin--.

In column 23, line 44, please delete "Chalfont Buckinghamshire", and insert --Chalfont, Buckinghamshire--.

CERTIFICATE OF CORRECTION (continued)
U.S. Pat. No. 7,645,449 B2

In column 24, line 30, please delete "Mass):", and insert --Mass).--.

In column 25, lines 4-5, please delete "immuno-globai", and insert --immunoglobulin--.

In column 25, line 41, please delete "plasmnids", and insert --plasmids--.

In column 25, line 42, please delete "calciumn", and insert --calcium--.

In column 25, lines 45-46, please delete "centri-flged", and insert --centrifuged--.

In column 25, line 46, please delete "32° C. and", and insert --32° C and--.

In column 26, line 1, delete "cytoldnes", and insert --cytokines--.

In column 28, claim 1, line 58, please delete "(IL)4", and insert --(IL) 4--.

In column 28, claim 1, line 62, please delete "non-lymphoid", and insert --non-myeloid--.

In column 29, claim 3, line 19, please delete "antibody that", and insert --antibody or fragment thereof that--.

In column 29, claim 4, line 24, please delete "antibody that", and insert --antibody or fragment thereof that--.

In column 29, claim 9, line 55, please delete "5-fluoro-2'-deoxyuiridine", and insert --5-fluoro-2'-deoxyuridine--.

In column 29, claim 9, line 59, please delete "puromnycin", and insert --puromycin--.

In column 29, claim 9, line 62, please delete "(7-hydroxystaurasporine)", and insert --(7-hydroxystaurosporine)--.

In column 29, claim 9, line 67, please delete "nimustrine, carmustrine", and insert --nimustine, carmustine--.

In column 30, claim 9, line 2, please delete "teosulfene", and insert --treosulfane--.

In column 30, claim 9, line 3, please delete "tremozolamide", and insert --temozolamide--.

In column 30, claim 9, line 5, please delete "tioguanine", and insert --thioguanine--.

In column 32, claim 58, line 65, please delete "minor", and insert --tumor--.

In column 33, claim 59, line 2, please delete "non-lymphoid", and insert --non-myeloid--.

UNITED STATES PATENT AND TRADEMARK OFFICE
CERTIFICATE OF CORRECTION

PATENT NO. : 7,645,449 B2
APPLICATION NO. : 10/544794
DATED : January 12, 2010
INVENTOR(S) : Stassi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 482 days.

Signed and Sealed this

Twenty-first Day of December, 2010

David J. Kappos
*Director of the United States Patent and Trademark Office*